(12) United States Patent
Maiti et al.

(10) Patent No.: US 10,977,398 B2
(45) Date of Patent: Apr. 13, 2021

(54) SYSTEMS AND METHODS FOR DETERMINING PROPERTIES OF COMPOSITE MATERIALS FOR PREDICTING BEHAVIOUR OF STRUCTURES

(71) Applicant: Tata Consultancy Services Limited, Mumbai (IN)

(72) Inventors: Soumyadipta Maiti, Pune (IN); Amit Gangadhar Salvi, Pune (IN); Beena Rai, Pune (IN); Shashank Mishra, Pune (IN); Suryanaman Chaube, Pune (IN); Purushottham Gautham Basavarsu, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 392 days.

(21) Appl. No.: 15/936,896

(22) Filed: Mar. 27, 2018

(65) Prior Publication Data

US 2019/0065645 A1 Feb. 28, 2019

(30) Foreign Application Priority Data

Aug. 24, 2017 (IN) .............................. 201721030095

(51) Int. Cl.
*G06F 30/23* (2020.01)
*G06Q 50/04* (2012.01)
(Continued)

(52) U.S. Cl.
CPC ............. *G06F 30/23* (2020.01); *G06Q 50/04* (2013.01); *G16C 60/00* (2019.02);
(Continued)

(58) Field of Classification Search
CPC ...... G06F 30/23; G06F 30/20; G06F 2113/26; G06F 30/17; G16C 60/00; G06Q 50/04; G01N 2033/0003
See application file for complete search history.

(56) References Cited

U.S. PATENT DOCUMENTS 6,212,485 B1 * 4/2001 Nakano .................. G16C 60/00
703/5
8,862,437 B1 10/2014 Rassaian et al.
(Continued)

FOREIGN PATENT DOCUMENTS

CN 105069241 A 11/2015

OTHER PUBLICATIONS

Liu, Shengyuan. "Hybrid Molecular Dynamics-Finite Element Simulations of Polystyrene-Silica Nanocomposites." PhD diss., Technische Universität Darmstadt, 2017. (Year: 2017).*

(Continued)

*Primary Examiner* — Chuen-Meei Gan
(74) *Attorney, Agent, or Firm* — Finnegan, Henderson, Farabow, Garrett & Dunner LLP

(57) ABSTRACT

Engineered structures include materials in certain arrangement and proportions to make a composite that provides desired properties to a structure. The mechanical and physical properties of the materials are measured through expensive and time consuming mechanical testing, and structural design is carried out using these properties thus warranting more time and cost spent on physical testing. Embodiments of the present disclosure provide multi-scale modeling and simulation techniques (MSMST) for design of composite materials with desired macro-scale properties wherein the (lower) MSMST are interconnected and each can pass on corresponding desired outputs to higher length-scales, which in turn evaluate macro-scale physical and mechanical properties/either to scale up the structure simulation, or to fine tune computational materials parameters thereby predicting behaviour of the structure based on determined properties of composite materials of the structure.

15 Claims, 17 Drawing Sheets

(51) Int. Cl.
G16C 60/00 (2019.01)
G01N 33/00 (2006.01)
G06F 30/17 (2020.01)
G06F 30/20 (2020.01)
G06F 113/26 (2020.01)

(52) U.S. Cl.
CPC ...... G01N 2033/0003 (2013.01); G06F 30/17 (2020.01); G06F 30/20 (2020.01); G06F 2113/26 (2020.01)

(56) References Cited

U.S. PATENT DOCUMENTS

2012/0108686 A1    5/2012  Verstraete et al.
2014/0309971 A1*  10/2014  Ueno .................. G16C 10/00
                                                                    703/2

OTHER PUBLICATIONS

Yang, B. J., H. Shin, Haeng-Ki Lee, and Hyungjun Kim. "A combined molecular dynamics/micromechanics/finite element approach for multiscale constitutive modeling of nanocomposites with interface effects." Applied Physics Letters 103, No. 24 (2013): 241903. (Year: 2013).*

Chaube, Suryanaman, Shashank Mishra, Soumyadipta Maiti, and Beena Rai. "Multiscale analysis of large-strain deformation behaviour of random cross-linked elastomers." Molecular Simulation 45, No. 2 (2019): 111-119. (Year: 2019).*

Sharma, Pragati, Sudip Roy, and Hossein Ali Karimi-Varzaneh. "Validation of force fields of rubber through glass-transition temperature calculation by microsecond atomic-scale molecular dynamics simulation." The Journal of Physical Chemistry B 120, No. 7 (2016): 1367-1379. (Year: 2016).*

Wang, Qiming, and Zheming Gao. "A constitutive model of nanocomposite hydrogels with nanoparticle crosslinkers." Journal of the Mechanics and Physics of Solids 94 (2016): 127-147. (Year: 2016).*

Mousavi, Atiyeh Alsadat, Behrouz Arash, Xiaoying Zhuang, and Timon Rabczuk. "A coarse-grained model for the elastic properties of cross linked short carbon nanotube/polymer composites." Composites Part B: Engineering 95 (2016): 404-411. (Year: 2016).*

Curgul, Sezen, Krystyn J. Van Vliet, and Gregory C. Rutledge. "Molecular dynamics simulation of size-dependent structural and thermal properties of polymer nanofibers." Macromolecules 40, No. 23 (2007): 8483-8489. (Year: 2007).*

Kantesh Balani "Physical, Thermal, and Mechanical Properties of Polymers" John Wiley & Sons, Inc Dec. 12, 2014 (Year: 2014).*

Pavan Kumar Valavala, "Multiscale constitutive modeling of polymer materials", Date: 2008, Publisher: Michigan Technological University Link: http://diaitalcommons.mtu.edu/cgi/viewcontent.coi?article=1416&context=etds.

* cited by examiner

SYSTEMS AND METHODS FOR DETERMINING PROPERTIES OF COMPOSITE MATERIALS FOR PREDICTING BEHAVIOUR OF STRUCTURES

PRIORITY CLAIM

This U.S. patent application claims priority under 35 U.S.C. § 119 to: India Application No. 201721030095, filed on Aug. 24, 2017. The entire contents of the aforementioned application are incorporated herein by reference.

TECHNICAL FIELD

The disclosure herein generally relate to multiscale modeling of composite materials, and, more particularly, to systems and methods for determining properties of composite materials for predicting behaviour of structures associated thereof.

BACKGROUND

Manmade engineered structures are made up of many materials such as metals, ceramics, polymers, etc. These materials are arranged in certain arrangement and proportions to make a composite that provides certain desired properties to the structure. The mechanical and physical properties of these materials are measured through expensive and time consuming mechanical testing and structural design is carried out using these properties. Many such materials are engineered to provide certain properties using nano and micro reinforcements in the form of fillers. Properties of such composites are altered by reinforcing materials, its volume fraction, and their interface, thus warranting an expensive set of physical tests at every scale of its development and qualification. The properties of such engineered materials are highly process dependent thus warranting more time and cost spent on physical testing. Existing methods/techniques involve large amount of time, and cost in material development and qualification.

SUMMARY

Embodiments of the present disclosure present technological improvements as solutions to one or more of the above-mentioned technical problems recognized by the inventors in conventional systems. For example, in one aspect, a computer implemented method for determining properties of composite materials for predicting behavior of a structure associated thereof is provided. The method, comprising: obtaining information pertaining to composite materials comprising at least one of one or more molecular and one or more nano-scale components of a structure; simulating the information pertaining to the one or more molecular and the one or more nano-scale components to obtain simulated data; performing, using a first Molecular Dynamics (MD) simulation technique, (i) a structural densification on the simulated data to obtain a densified structure output, and (ii) an equilibration technique on the densified structure output to determine an equilibration of the structure; simulating the densified structure output to determine at least one of (i) one or more relevant mechanical properties from a set of mechanical properties and (ii) one or more relevant thermal properties from a set of thermal properties and (iii) one or more thermodynamic properties; performing, a Constitutive Analytical Modeling (CAM) simulation technique, on the one or more relevant mechanical properties to obtain one or more CAM outputs; performing, a second MD simulation technique, on (i) the one or more relevant mechanical properties and the one or more relevant thermal properties, (ii) the one or more CAM outputs and (iii) the one or more thermodynamic properties to generate one or more second MD outputs; and performing, a Finite Element Analysis (FEA) modeling, on at least some of (i) the one or more relevant mechanical properties and the one or more relevant thermal properties, (ii) the one or more CAM outputs, and the one or more second MD outputs to predict a behaviour of the structure. In an embodiment, the behaviour of the structure is predicted based on the densified structure output, and the determined equilibration of the structure.

In an embodiment, the one or more relevant mechanical properties from a set of mechanical properties may comprise Non-equilibrium molecular dynamics (NEMD) method derived nano fracture, cyclic stress-strain, pressure response, Nano-filler dispersion, and phase-interface strength.

In an embodiment, the one or more relevant thermal properties from the set of thermal properties may comprise thermal expansion, heat conduction and phonon, and wherein the one or more thermodynamic properties comprise thermodynamics derived cohesive energy.

In an embodiment, the one or more CAM outputs may comprise equilibrium stress-strain and elastic moduli, cyclic loading analysis of polymer matrix composites, Payne and Mullins effects, stress-strain hysteresis with one or more strain rates.

In an embodiment, the first MD simulation technique comprises an all-atomistic MD simulation technique and the second MD simulation technique comprises a Coarse-graining molecular dynamics (CGMD) simulation technique. In an embodiment, the one or more second MD outputs comprise equilibrium and non-equilibrium stress-strain relations, Dynamic mechanical analysis (DMA), local micro structural evolution, localized fracture, Radial distribution function (RDF) and Glass transition temperature (GTT), and one or more inputs for Dissipative particle dynamics-second MD (DPD-SMD) simulation technique.

In another aspect, a system for determining properties of composite materials for predicting behavior of a structure associated thereof is provided. The system comprising: a memory storing instructions; one or more communication interfaces; and one or more hardware processors coupled to the memory (102) via the one or more communication interfaces, wherein the one or more hardware processors (104) are configured by the instructions to: obtain, information pertaining to composite materials comprising at least one of one or more molecular and one or more nano-scale components of a structure; simulate the information pertaining to the one or more molecular and the one or more nano-scale components to obtain simulated data; perform, using a first Molecular Dynamics (MD) simulation technique, (i) a structural densification on the simulated data to obtain a densified structure output, and (ii) an equilibration technique on the densified structure output to determine an equilibration of the structure; simulate the densified structure output to determine at least one of (i) one or more relevant mechanical properties from a set of mechanical properties and (ii) one or more relevant thermal properties from a set of thermal properties and (iii) one or more thermodynamic properties; perform, a Constitutive Analytical Modeling (CAM) simulation technique, on the one or more relevant mechanical properties to obtain one or more CAM outputs; perform, a second MD simulation technique, on (i) the one or more relevant mechanical properties and the one or more relevant thermal properties, (ii) the one or more CAM outputs and (iii) the one or more thermodynamic properties; to generate one or more second MD outputs; and perform, a Finite Element Analysis (FEA) modeling, on at least some of (i) the one or more relevant mechanical properties and the one or more relevant thermal properties, (ii) the one or more CAM outputs, and the one or more second MD outputs to predict a behaviour of the structure. In an embodiment, the behaviour of the structure is predicted based on the densified structure output, and the determined equilibration of the structure.

In an embodiment, the one or more relevant mechanical properties from a set of mechanical properties may comprise Non-equilibrium molecular dynamics (NEMD) and Nano fracture, cyclic stress-strain, pressure response, Nano-filler dispersion, and phase-interface strength.

In an embodiment, the one or more relevant thermal properties from the set of thermal properties may comprise thermal expansion, heat conduction and phonon, and wherein the one or more thermodynamic properties comprise thermodynamics derived cohesive energy.

In an embodiment, the one or more CAM outputs may comprise equilibrium stress-strain and elastic moduli, cyclic loading analysis of polymer matrix composites, Payne and Mullins effects, stress-strain hysteresis with one or more strain rates.

In an embodiment, the first MD simulation technique comprises an all-atomistic MD simulation technique and the second MD simulation technique comprises a Coarse-graining molecular dynamics (CGMD) simulation technique. In an embodiment, the one or more second MD outputs comprise equilibrium and non-equilibrium stress-strain, Dynamic mechanical analysis (DMA), local micro structural evolution, localized fracture, Radial distribution function (RDF) and Glass transition temperature (GTT), and one or more inputs for Dissipative particle dynamics-second MD (DPD-SMD) simulation technique.

In yet another one aspect, one or more non-transitory machine readable information storage mediums comprising one or more instructions is provided. The one or more instructions which when executed by one or more hardware processors causes predicting behavior of a structure associated thereof by: obtaining information pertaining to composite materials comprising at least one of one or more molecular and one or more nano-scale components of a structure; simulating the information pertaining to the one or more molecular and the one or more nano-scale components to obtain simulated data; performing, using a first Molecular Dynamics (MD) simulation technique, (i) a structural densification on the simulated data to obtain a densified structure output, and (ii) an equilibration technique on the densified structure output to determine an equilibration of the structure; simulating the densified structure output to determine at least one of (i) one or more relevant mechanical properties from a set of mechanical properties and (ii) one or more relevant thermal properties from a set of thermal properties and (iii) one or more thermodynamic properties; performing, a Constitutive Analytical Modeling (CAM) simulation technique, on the one or more relevant mechanical properties to obtain one or more CAM outputs; performing, a second MD simulation technique, on (i) the one or more relevant mechanical properties and the one or more relevant thermal properties, (ii) the one or more CAM outputs and (iii) the one or more thermodynamic properties to generate one or more second MD outputs; and performing, a Finite Element Analysis (FEA) modeling, on at least some of (i) the one or more relevant mechanical properties and the one or more relevant thermal properties, (ii) the one or more CAM outputs, and the one or more second MD outputs to predict a behaviour of the structure. In an embodiment, the behaviour of the structure is predicted based on the densified structure output, and the determined equilibration of the structure.

In an embodiment, the one or more relevant mechanical properties from a set of mechanical properties may comprise Non-equilibrium molecular dynamics (NEMD) related/obtained Nano fracture, cyclic stress-strain, pressure response, Nano-filler dispersion, and phase-interface strength.

In an embodiment, the one or more relevant thermal properties from the set of thermal properties may comprise thermal expansion, heat conduction and phonon, and wherein the one or more thermodynamic properties comprise thermodynamics derived cohesive energy.

In an embodiment, the one or more CAM outputs may comprise equilibrium stress-strain and elastic moduli, cyclic loading analysis of polymer matrix composites, Payne and Mullins effects, stress-strain hysteresis with one or more strain rates.

In an embodiment, the first MD simulation technique comprises an all-atomistic MD simulation technique and the second MD simulation technique comprises a Coarse-graining molecular dynamics (CGMD) simulation technique. In an embodiment, the one or more second MD outputs comprise equilibrium and non-equilibrium stress-strain, Dynamic mechanical analysis (DMA), local micro structural evolution, localized fracture, Radial distribution function (RDF) and Glass transition temperature (GTT), and one or more inputs for Dissipative particle dynamics-second MD (DPD-SMD) simulation technique.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
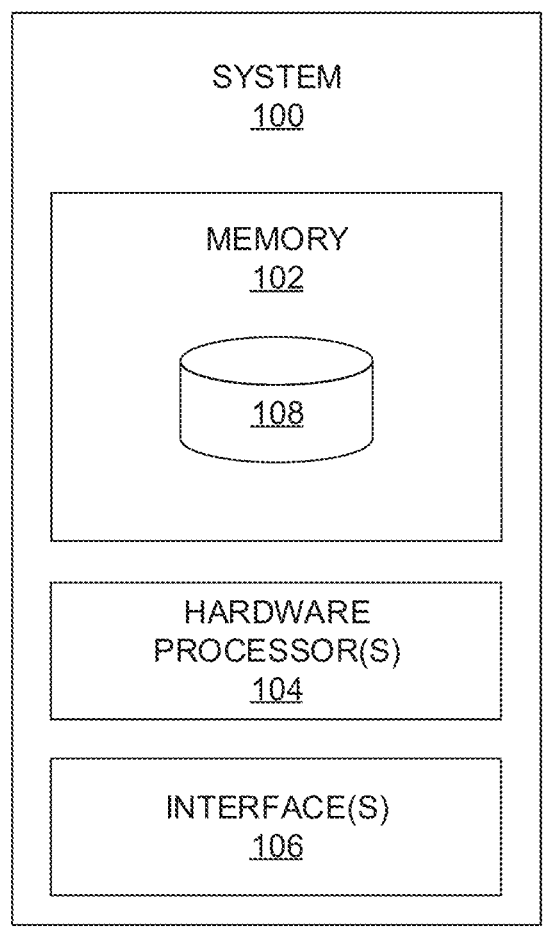
FIG. 1 illustrates an exemplary block diagram of a system for determining properties of composite materials in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Engineered structures include materials in certain arrangement and proportions to make a composite that provides desired properties to a structure. The mechanical and physical properties of the materials are measured through expensive and time consuming mechanical testing, and structural design is carried out using these properties thus warranting more time and cost spent on physical testing. Embodiments of the present disclosure provide multi-scale. Embodiments of the present disclosure implement multi-scale modeling procedure for design of composite materials with desired macro-scale properties from a set of lower length-scale modeling and simulations (e.g., starting from all-atomistic molecular dynamics (MD)). These different multi-scale modeling techniques, for example, but are not limited to, an all-atomistic MD, a coarse graining MD (CGMD), constitutive and phenomenological modeling, finite element modeling (FEM) of single-phase and composite structures are interconnected and different modeling and simulation techniques can pass on important parameters to higher length-scales, which in turn evaluate macro-scale physical and mechanical properties. Each of the mentioned techniques may pass on certain computed parameters to higher and lower length scale, either to scale up the structure simulation, or to fine tune computational materials parameters. This makes the whole mechanism a bottom-up and top-down hierarchical and concurrent simulation platform for various materials such as metals, polymers etc.

Moreover, the embodiments of the present disclosure provide systems and methods that implement an engineering approach to design composite materials by modeling constituent materials from atomistic simulations till continuum scale simulations. The behavior of the materials under various conditions can be modelled from its molecular scale all the way up to macro scale through various intermediate scales, thus saving on time and cost of development. Thus, by combining high fidelity computational and analytical techniques, properties of materials can be predicted that can be used in performance analysis of the large engineered structures.

Referring now to the drawings, and more particularly to FIGS. 1 through 17, where similar reference characters denote corresponding features consistently throughout the figures, there are shown preferred embodiments and these embodiments are described in the context of the following exemplary system and/or method.

FIG. 1 illustrates an exemplary block diagram of a system 100 for determining properties of composite materials in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the device 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment a database 108 can be stored in the memory 102, wherein the database 108 may comprise, but are not limited to information pertaining to composite materials comprising at least one of one or more molecular and one or more nano-scale components of a structure, output(s) generated by one or more simulation technique(s), one or more modeling technique(s), etc. In an embodiment, the memory 102 may store the one or more modeling technique(s), the one or more simulation technique(s), which are executed by the one or more hardware processors 104 to perform the methodology described herein.

Figure 2:
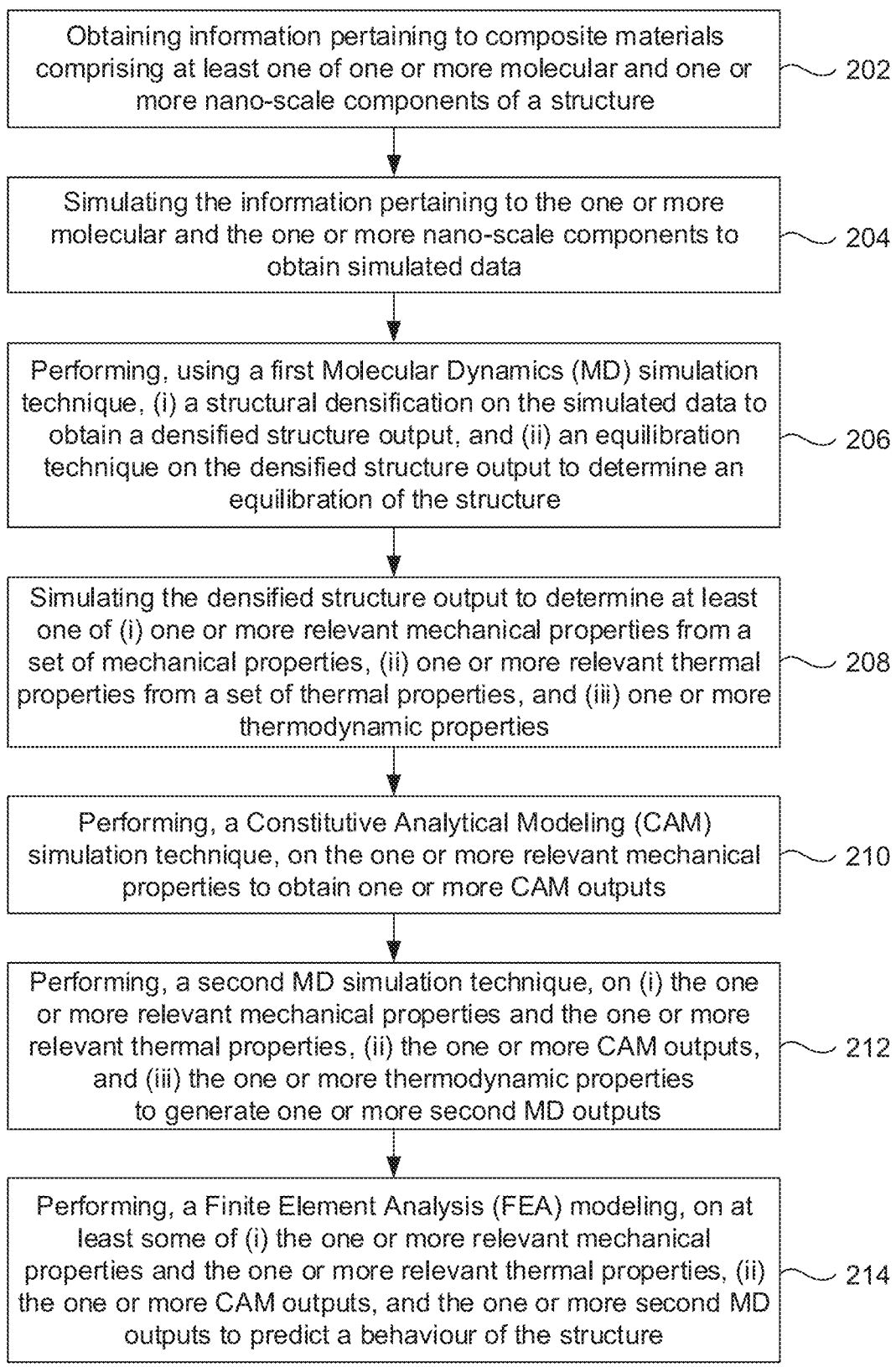
FIG. 2 illustrates an exemplary flow diagram of a method for determining properties of composite materials using the system of FIG. 1 in accordance with an embodiment of the present disclosure.

FIG. 2, with reference to FIG. 1, illustrates an exemplary flow diagram of a method for determining properties of composite materials using the system 100 of FIG. 1 in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIG. 1, and the flow diagram. In an embodiment of the present disclosure, at step 202, the one or more hardware processors 104 obtain information pertaining to composite materials comprising at least one of one or more molecular and one or more nano-scale components of a structure. In an embodiment, the structures, for example, may be of polymer matrix composite type wherein polymers can be crosslinked, uncrosslinked, thermoplastic or thermosetting type. Fillers can be organic/inorganic/metal particles and/or fibers. In another embodiment, the structure can be generated in various packages, for example, LAMMPS, Materials Studio, Packmol, Gulp or by writing customized scripts for ordinary and complex crosslinked polymer matrix composites. Initial density of the structures may be orders of magnitude lower than the final density. Typically the all-atomistic simulation structures take atoms from few thousands to a few millions (e.g., million atoms, 1-500 nm range). The system size analyzed here are less than 500 nm in dimension.

In an embodiment of the present disclosure, at step 204, the one or more hardware processors 104 simulate, (using all-atomistic molecular dynamics technique(s), the information pertaining to the one or more molecular and the one or more nano-scale components to obtain simulated data. In an embodiment of the present disclosure, at step 206, the one or more hardware processors 104 perform, using a first Molecular Dynamics (MD) technique, (i) a structural densification on the simulated data to obtain a densified structure output, and (ii) an equilibration technique on the densified structure output to determine an equilibration of the structure.

In an embodiment of the present disclosure, at step 208, the one or more hardware processors 104 simulate the densified structure output to determine at least one of (i) one or more relevant mechanical properties from a set of mechanical properties (ii) one or more relevant thermal properties from a set of thermal properties, and (iii) one or more relevant thermodynamic properties from a set of thermodynamic properties. In an embodiment, the initial structures are densified by constant temperature-pressure (NPT) run. More advanced techniques for example, but not limited to, simulated annealing etc., can also be used for this structural densification. Typically the MD simulations should be run for a few nanoseconds to achieve maximum density. In an embodiment of the present disclosure, the one or more relevant mechanical properties from the set of mechanical properties may comprise, but are not limited to, NEMD (Non-equilibrium molecular dynamics) and nano fracture, Cyclic stress-strain, pressure response, Nano-filler dispersion, phase-interface strength, etc. In an example, phase interface is an interface/joining boundary between two components in a composite structure.

In NEMD simulation, system (structure) is subjected to high strain rate deformations by loading in many different ways for example, indentation, tension, compression, shear, etc. The temperature of the system is usually under control to desired value. Severe strain causes local structural damage resulting in fractured surfaces, Nano-cavity, delamination, etc. In cyclic stress-strain simulations, the system is deformed with sinusoidal strain in uniaxial, biaxial or shear loading conditions. The stress response is noted and analyzed for storage modulus (G'), loss modulus (G"), tan ($\delta$) loss factor altogether giving the dynamic mechanical analysis (DMA).

Polymeric matrix materials display an instantaneous and a time dependent stress relaxation behavior. By performing NPT relaxations on the systems for less than 50 ns simulation time, an instantaneous stress-strain pressure response curve can be generated. In Nano filler dispersion, polymer matrix nano composite materials have dispersed filler particles which can move and rearrange by thermal motions and different types of external mechanical loading conditions. The dispersed particles can indicate difference in the dispersion pattern for example, agglomeration, percolating structure etc. after MD simulations are carried out for a predetermined time. In phase-interface strength simulation, one particular polymer matrix composite can be touching or embedding other different-phase surfaces or fibers. With MD simulations, the fracture toughness, cohesive strength of two-phase interface can be calculated under different loading conditions, for example, but are not limited to, tension, shear or fiber pull out from the polymer matrix.

In another embodiment, the one or more relevant thermal properties from the set of thermal properties comprise but are not limited to, thermal expansion, heat conduction and phonon, and wherein the one or more relevant thermodynamic properties from a set of thermodynamic properties may comprise, but is not limited to, thermodynamics derived cohesive energy.

Thermal expansion: By running NPT relaxation simulations, the equilibrium volume of the systems is reached in a few nanosecond of MD run. The equilibrium volume change with different temperatures would give the thermal expansion coefficient. Change in the trend of thermal expansion behavior can also suggest physical change in the studied structure, for example, a transition from glassy to rubbery or rubbery to viscous transition.

Heat conduction and Phonon: By running all-atomistic MD simulations of the studied system, phonon density of states of single or multiple phases can be calculated. This in turn gives specific heat of the different phases present in the system. By velocity autocorrelation analysis of the thermalized system, the heat transfer coefficients can also be obtained.

Thermodynamics derived cohesive energy: From MD simulation runs, internal energy change in terms of potential energy can be obtained. Internal energy change between different configurations can be used to calculate the energy of free surfaces, two-phase interfaces, etc. Also change in energy due to bonded and non-bonded interactions between polymer/monomer units can be obtained as different types of cohesive energies. Cohesive energy calculated for monomer units can be passed on to Dissipative particle dynamics CGMD (DPD-CGMD) as well.

Referring back to steps of FIG. 2, in an embodiment of the present disclosure, at step 210, the one or more hardware processors 104 perform, a Constitutive Analytical Modeling (CAM) technique, on the one or more relevant mechanical properties to obtain one or more CAM outputs. In CAM technique, bulk equilibrium and dynamic properties are analytically solved based on different kinds of phenomenological models. The input parameters are obtained from the densified and crosslinked MD generated structures. The one or more CAM outputs, may comprise but are not limited to, equilibrium stress-strain and elastic moduli, Cyclic loading analysis of polymer matrix composites, Payne and Mullins effects, stress-strain hysteresis with different strain rates, etc.

Equilibrium stress-strain and elastic moduli: For equilibrium stress-strain and elastic moduli, equilibrium stress-strain relationships of crosslinked elastomer polymers based materials are calculated with the inputs from all-atomistic MD. The parameters passed on are: volumetric polymer segment density, number of linking elements (Kuhn lengths) per crosslinked polymer segments and temperature of the system. The strain energy equations are derived from the underlying structure of long molecular chains and through configurational entropy of the system. Stress-strain relationships and corresponding elastic moduli can be obtained for uniaxial, biaxial and shear deformations.

Cyclic loading analysis, Payne and Mullins effects: Payne effect refers to a significant decrease in the storage modulus and a maximum in loss modulus of particle-reinforced elastomers with an increase in the amplitude of mechanical oscillations. Mullins effect refers to the initial stress softening during the loading cycles before reaching the steady hysteresis cycles. These effects on the mechanical properties are calculated based on inputs from the structure and MD simulation for example, but are not limited to, filler volume fraction, crosslinking density, volumetric number density of chain segments, interfacial bonding energy between filler and polymer matrix, interfacial friction, etc.

Hysteresis effects: Under stress-strain loading and unloading cycle at a particular strain rate the polymer composite system can be assumed to follow two or more different behavior: an equilibrium response and a time-dependent deviation from equilibrium suggesting that the material can be modeled as two polymer networks acting in parallel causing a hysteresis effect. This effect can be analytically captured by Reptation dynamics scaling laws. Parameters, for example, but not limited to, the Rouse relaxation time and polymeric tube disentanglement time may be estimated from MD and fed into the constitutive model (or CAM technique).

Referring back to steps, in an embodiment of the present disclosure, at step 212, the one or more hardware processors 104 perform, a second MD technique, on (i) the one or more relevant mechanical properties and the one or more relevant thermal properties, (ii) the one or more CAM outputs to generate one or more second MD outputs. In an embodiment the one or more second MD outputs (or the CGMD outputs), comprise but are not limited to, Equilibrium and non-equilibrium stress-strain, DMA, local micro structural evolution, localized fracture, RDF and GTT, and one or more inputs for DPD-CGMD, etc.

The second MD technique (or second MD simulation) is a coarse grain molecular dynamics (CGMD) technique. In an embodiment, in the CGMD simulations, more than 10 atoms of a few adjacent monomers are clubbed (or merged) together as a coarse bead. This treatment effectively can allow to simulate 'n' times bigger systems than that possible by all-atomistic MD wherein 'n' may be 100. Polymer composite system sizes up to micrometer range can be simulated by this technique. Structural, mechanical and thermal parameters obtained from the all-atomistic MD and CAM technique are passed onto the CGMD simulations. CGMD interaction potentials are custom developed and fine-tuned to reproduce values and trends of different properties obtained from all-atomistic MD and CAM. Below are examples of the important passed on parameters from all-atomic MD simulation technique to CGMD simulation technique:

Density: In all-atomistic MD, the composite densified structure provides the densities of individual component phases. The CGMD simulations may reproduce correct (and/or acceptable) level of density of the simulated systems.

Radial distribution function (RDF): RDF gives the average number of neighboring atoms present with respect to (hereinafter referred as 'w.r.t') radial distance to a particular atom type. Essentially, a fine-tuned proper CGMD interaction potentials are able to reproduce the same/similar RDF that is obtained from all-atomistic MD technique.

Stress-strain relations: By performing NEMD and pressure response simulations in all-atomistic MD, various types of stress-strain relationships are obtained for different types of crosslinked and Nano composite structures. CGMD simulation techniques essentially reproduce the trends of stress-strain relationships and local deformation observed in all-atomistic MD technique's output.

Kuhn length: A flexible polymer chain can be assumed to be consisting of a number of connected segments (beads) forming a long random walk structure. The bead size is usually associated with the Kuhn segment length, which can be obtained from the spatial autocorrelation function or radius of gyration calculation done on polymeric chain structures obtained from all-atomistic MD technique's output. The calculated Kuhn length can be used as a coarse-graining bead diameter for CGMD and DPD.

Coefficient of thermal expansion (COTE) and Glass transition temperature (GTT): COTE is calculated from the equilibrium system volume from NPT MD runs. GTT is identified as transition region of COTE between two phases. The COTE and GTT obtained from the CGMD simulation technique is compared with the similar value(s)/trends obtained from the all-atomistic MD technique's output for validation of the CGMD interaction potentials.

Following are the parameters/outputs passed from CAM simulation technique to CGMD simulation technique:

Equilibrium stress-strain relations: CAM simulation technique generates equilibrium stress-strain relation curves under uniaxial, biaxial and shear loading conditions. Whereas NPT simulations by CGMD simulation technique produces equilibrium stress response w.r.t external applied load/pressure. The equilibrium stress-strain curves obtained from CGMD simulation technique are compared with those from CAM simulation technique to evaluate the quality of the potentials being developed.

DMA effects: Constitutive phenomenological models can produce mechanical stress response of cyclic loading with varying strain amplitude and filler fractions as in Payne and Mullins effects. Proper/appropriate CGMD potentials developed for polymers and filler particles reproduce the variation storage and loss modulus under different kinds of cyclic dynamic loading conditions.

The second MD outputs generated are provided by way of examples below, and shall not be construe as limiting the scope of the embodiments of the present disclosure:

Equilibrium and non-equilibrium stress-strain: By CGMD simulation, equilibrium stress-strain relaxation can be achieved by NPT as the simulations can be run for microsecond timescales for micrometer length scale structures. Medium and high strain-rate non-equilibrium stress-strain relations are also obtained by the CGMD simulations of polymer composites.

DMA: Similar to all-atomistic MD, CGMD provides results of DMA of large (up to micron scale) composite structures such as storage and loss moduli, frequency and oscillation amplitude dependent response. Dynamic moduli variations due to Payne and Mullins effects of polymer matrix composites may be obtained.

Local microstructural evolution: Polymer matrix composites comprise disperse particles or fibers which can move at the Nano and micron level under thermal, chemical and applied external forces. CGMD simulation techniques capture all these effects under NPT, NVT, constant strain rate deformation and cyclic dynamic loading conditions. Different kinds of local micro structural features of dispersed phases, for example, agglomeration, deagglomeration, bands, stratification, Nano and micro-cavity formation may be simulated.

Localized fracture: CGMD simulation technique performed under high levels of loading either by NPT or NEMD can simulate local fracture behaviour. Fracture behaviour can be identified with creation of Nano/micron sized voids, stress level shooting up to create local bond breakage or bond distances exceeding certain values. In addition to the initiation of fracture, CGMD simulation technique enables studying crack propagation, movement and arrangement of filler particles during fracture.

RDF and GTT: Similar to all-atomistic MD, the CGMD simulation technique provides the RDF of different components of the polymer composite w.r.t other component/feature. This RDF in CGMD encompasses much larger length scale and can provide new features such as nature of agglomeration or dispersion among filler particles, etc. GTT analysis by the CGMD simulation technique (similar to all-atomistic MD simulation technique) provides the change in glassy to rubbery behaviour of polymer composites by equilibrium NPT run. Alternatively GTT can also be determined by DMA at different frequencies for different kinds of polymer composites.

Inputs for DPD-CGMD: In DPD simulations, the bonded interactions and the initial bead sizes can be obtained from the CGMD simulation technique's output. The quality of the DPD interactions with all the conservation, dissipative and random forces acting together can be determined from the CGMD structural and mechanical results, for example, RDF, DMA, stress-strain analysis, etc. Once the initial DPD interaction parameters are finalized, coarser grains in DPD can be accounted for creating micron scale structures for rheological and DMA studies.

Referring back to steps, in an embodiment of the present disclosure, at step 214, the one or more hardware processors 104 perform, a Finite Element Analysis (FEA) modeling, on at least some of (i) the one or more relevant mechanical properties and the one or more relevant thermal properties, (ii) the one or more CAM outputs, and the one or more second MD outputs to generate one or more FEA outputs that are used to predict a behaviour of the structure. In an embodiment of the present disclosure, the one or more hardware processors 104 also take into account densified structure output, and equilibration while performing the Finite Element Analysis (FEA) modeling, on at least some of (i) the one or more relevant mechanical properties and the one or more relevant thermal properties, (ii) the one or more CAM outputs, and the one or more second MD outputs to predict a behaviour of the structure. In an embodiment, FEA modeling is a numerical technique of solving engineering and physics problems which include different processes for example pre-process which comprise the component geometric definition, material properties assigned and also applying appropriate loads and boundary conditions, followed by a solver in which a numerical technique is applied to solve the governing expressions (or equation(s)). Then a post-process is implemented to visualize one or more results.

Following are examples of one or more parameters/outputs from the above simulation techniques used in the FEA modeling to predict a behaviour of the structure:

Individual constituent and interfacial properties: A composite material is a heterogeneous material made up of different materials, mainly, a reinforcement material bonded by a matrix material. The composite made of these constituents has its own unique mechanical and physical properties which are dependent on individual constituents (material) properties and their interaction (system) properties.

Local composite microstructure: The composite properties are also dependent on the arrangement of its constituents and their volume fractions. For example, properties of the long fiber reinforced composite are dependent of the fiber architecture (unidirectional or multi-directional). In metallic systems, the properties are dependent on the constituent's phases or the microstructure. Microstructure may be structured or unstructured depending on the manufacturing processes and material system.

Multiscale analysis: Local microstructure to Global bulk: As the macro properties and damage is dependent on the local microstructure, multiscale analysis is used to study the dependence of global bulk behaviour on local microstructure and vice-versa. It is an analysis technique used to measure bulk properties based on physics and chemistry based modeling of phenomenon at small length scales. Multiple levels of (hierarchical) multiscale can be modeled to capture the bulk properties accurately.

Homogenization versus discretization: These are the different approaches usually used for multiscale analysis. Homogenization essentially is a bottom up approach in which the macro properties are predicted by modeling the local microstructures. On the other hand, discretization is a top down approach in which a bulk is divided into small blocks and then property of individual blocks are incorporated as per requirements at macro level.

The one or more FEA outputs are illustrated by way of examples below:

Structural response at macro level: The macro level response for example, deflection and stresses of the structure component are obtained by performing the FEA modeling.

Design optimization based on local microstructure, process parameters: The local microstructure of material is dependent on manufacturing or process parameters. Thus, the bulk properties of the structure (or materials) under predict behaviour can be tailored and optimized based on process parameters through microstructure engineering.

Design validation through experimentation: The obtained FEA outputs need to be validated with experimental results for validation. Conversely, high fidelity FE analysis of virtual tests are carried out on large assemblies and compared with experiments to validate individual constituents (materials) of the assembly.

Interfacial failure through cohesive analysis: A cohesive element analysis can be used to model interfacial failure at multiple interfaces.

Damage and failure analysis: Non-linearity in the response at the macro (bulk) level is caused by damage at the local level. Damage and failure analysis modeled at microstructure can capture the response accurately.

It is to be noted that embodiments of the present disclosure and the system 100 enable to obtain one or more outputs from other system(s) wherein the steps 202 till 212 may be performed in the other system(s) and the portion of the one of more output(s) of these steps 202 till 212 may be fed to step 214 to perform FEA modeling and to generate FEA output(s) that helps in predicting the behaviour of the structure. For instances, each of the steps 202-till 212 may be performed in a first system, and the step 214 may be performed in a second system wherein the step 214 utilizes output(s) of the steps 202 till 212 performed in the first system. Similarly, the system 100 may utilize output of steps 202 till 2012 performed (using the above mentioned simulation and modeling techniques) in one or more other systems to generate FEA output(s) for predicting behavior of the structure.

Experimental Validation of the Simulation:

In this study the properties of SBR1502 rubber was calculated using multiscale modelling technique. Initially, all atomistic molecular dynamics simulations were carried on this rubber material. The polymeric chain in this material consists of monomers namely cis-1, 4 butadiene, trans-1, 4 butadiene, 1, 2 butadiene and styrene. Each polymeric chain consists of 23.5 wt (weight) % of styrene, 55 wt % of trans-1, 4-butadiene, 9.5 wt % of cis-1, 4-butadiene and 12 wt % of 1, 2-butadiene. The molecular weight of each polymeric chain in SBR1502 was 91,350 g/mol. The crosslinking agent was disulphur molecule because the disulphidic linkage is one of the prominent linkage in the material. The sulphur concentration was taken as 0.5 phr so that the crosslinker density can match a typical value as reported. For the system consisting of filler particle, a hollow particle of 6 nm consisting of carbon atoms was constructed so that the density of these filler particles match reported values. The glass transition temperature and the density of SBR1502 rubber are 235.5K and 0.935 g/cc respectively. The crosslinking density for this rubber system with 0.5 phr concentration of sulphur molecule is $5.9*10^{-5}$ mol/cc.

Model Structure Input and Methodology:

For the system without filler particles, a system consisting of 5 polymeric chains with composition as given above along with 30 sulphur molecules was made at a very low density of 0.001. The forcefield used for all-atomistic molecular dynamics was PCFF (Polymer Consistent ForceField) and the timestep used was 1 fs. Then the system was subjected to NPT simulation to densify the system and later the vulcanisation was carried out by making extra carbon-sulphur bonds. After this, simulated annealing of the system was carried from temperature 300K to 600K and then it was again cooled down to 300K. The final density achieved was 0.865 g/cc and the observed crosslinking density is $5.3*10^{-5}$ mol/cc. Now, this system was equilibrated at various temperatures ranging from 50K to 480K using NVT ensemble and the specific volume was calculated at these temperatures. From the curve between specific volume and temperature the glass transition temperature was calculated.

For the coarse-graining molecular dynamics (CGMD) simulations, FENE (finite extensible nonlinear elastic) model of polymer chain was used which contained 30 beads each of mass m and diameter d. The system consisted of 400 polymeric chains and 800 crosslinker beads (each of mass m and diameter d). For the system containing filler particles, 30 filler beads were added into the system each of mass 64 m and diameter 4d.

Both all-atomistic MD and coarse-graining MD provide us with mechanical property response. With the help of all-atomistic MD, non-equilibrium molecular dynamics (NEMD) at high strain rate ($10^{10}$/sec) and (DMA) at a high frequency ($5*10^9$ Hz) and various temperature were performed. DMA provides us with storage and loss moduli at a particular cyclic vibration frequency and temperature. By applying time-temperature superposition principle on the simulated data, DMA response of a wide frequency range ($10$-$10^{16}$) Hz at a particular reference temperature were obtained and compared with conventional methodology data.

NEMD simulations (both all-atomistic MD and CGMD) are particularly helpful in observing local structural changes like rearrangement of filler particles in rubber matrix, effect of large strain, strain rates and local fracture. Some related simulation results on these aspects are also presented in the subsequent sections. Some equilibrium stress-strain property analysis can be done by subjecting the systems to NPT equilibration to different pressures. But this might not be fully achievable in all-atomistic MD. To calculate the equilibrium mechanical properties constitutive analytical modelling (CAM) methods are particularly helpful.

For CAM modelling of the studied system, a few parameters such as volume of the crosslinked rubber, number of polymer segments and number of crosslinkers per polymer chains and temperature are passed on as input. CAM modelling then generates equilibrium mechanical properties such as stress-strain curve for uniaxial, biaxial and pure shear type loading and the different corresponding elastic moduli.

Figure 3:
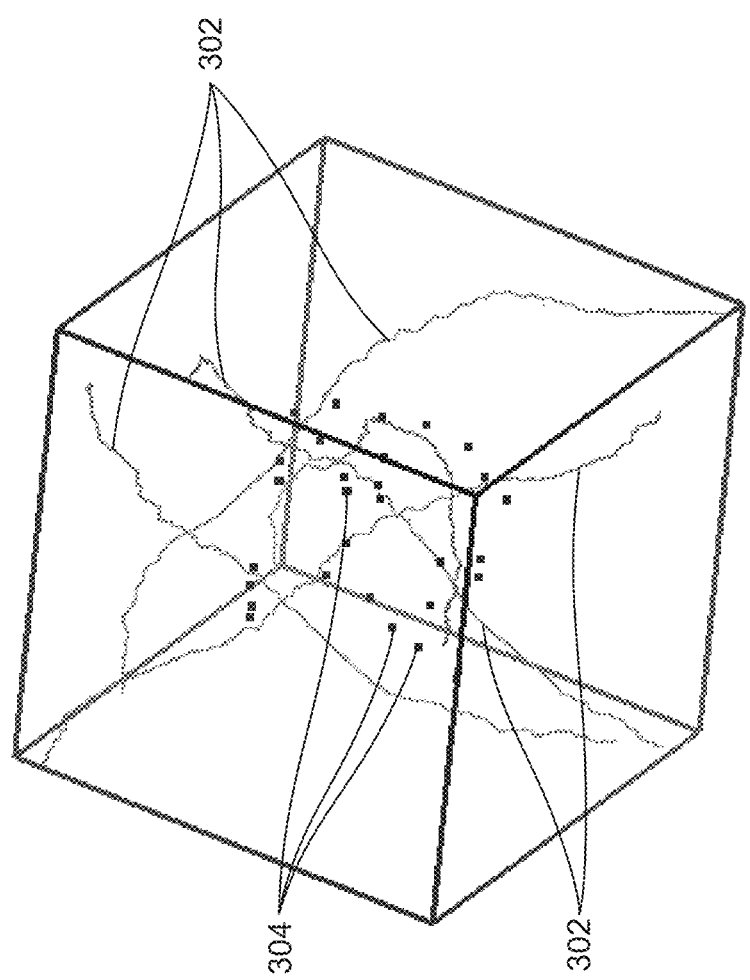
FIG. 3 depicts an input structure for multiscale modelling of a crosslinked rubber system in accordance with an example embodiment of the present disclosure.

FIG. 3, with reference to FIGS. 1-2, depict an initial input structure for a SBR 1502 rubber system has been created in accordance to an example embodiment of the present disclosure. More particularly, FIG. 3 depicts an input structure for multiscale modelling of a crosslinked rubber system in accordance with an example embodiment of the present disclosure. The 5 dark gray lines (denoted by 302 in FIG. 3) are polymer chains (molecular weight around 90,000 g/mol, 1500 (approx) monomer in each chain) and black (square) dots (denoted by 304 in FIG. 3) are disulphide crosslinker molecules. Density of initial structure (made by LAMMPS/Packmol/Materials Studio packages) can be orders of magnitude lower than the final output structure.

Multiscale Modelling Output:

Multiscale modelling output on the trial SBR 1502 rubber system has been presented wherein how the multiscale modelling methodology has been applied to obtain various local structural properties influencing the bulk property is depicted.

Figure 4:
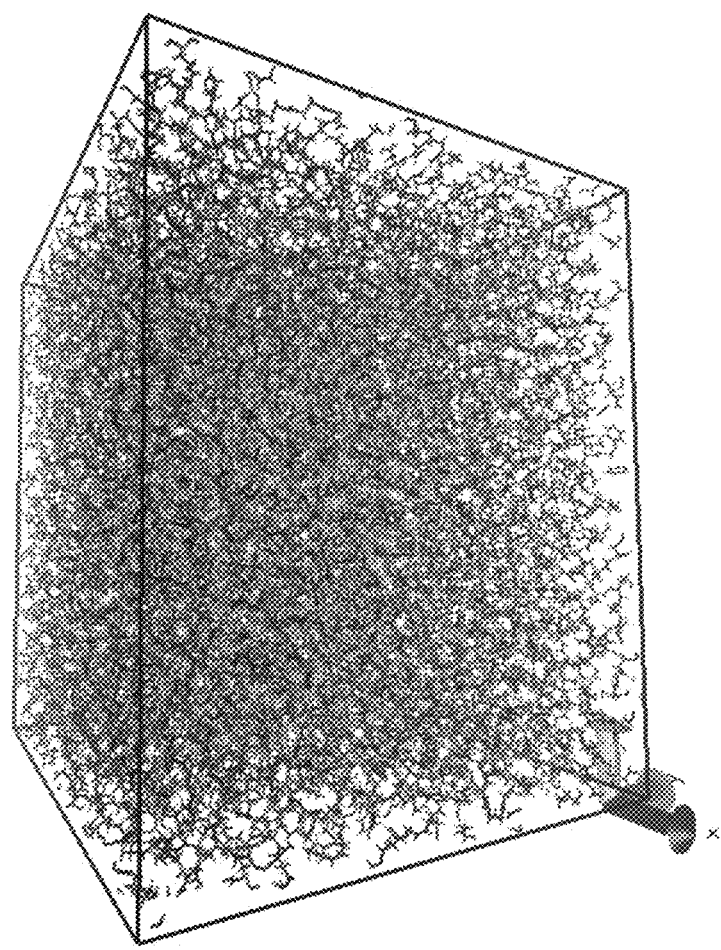
FIG. 4 depicts an all-atomistic structure of densified crosslinked SBR rubber system in accordance with an example embodiment of the present disclosure.
Figure 5:
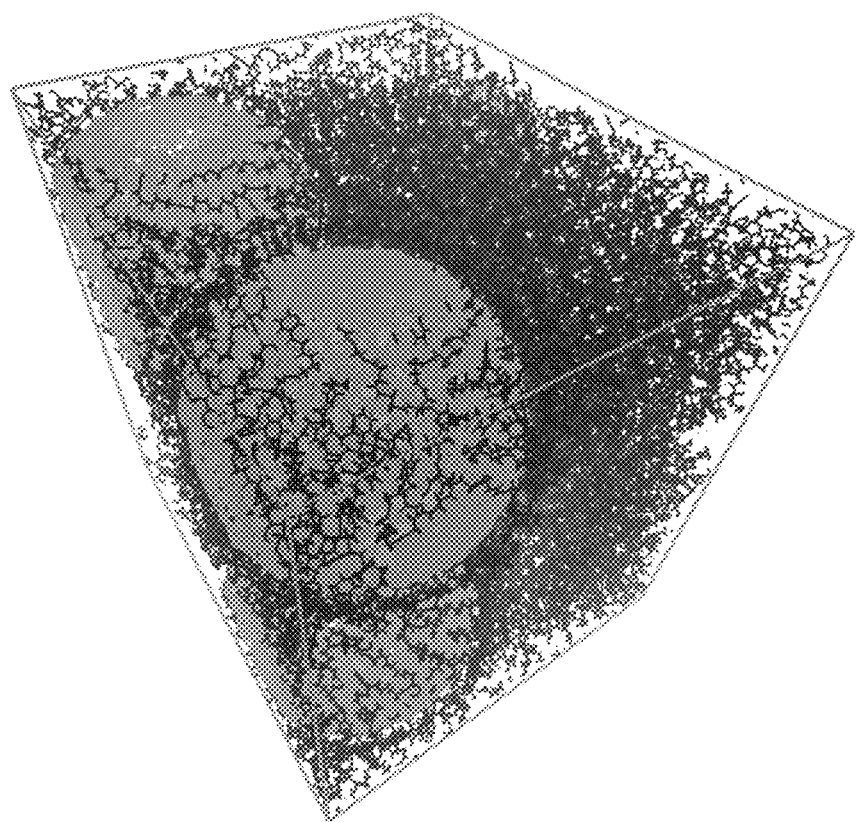
FIG. 5 depicts an all-atomistic local structure of a densified particle filled rubber matrix composite in accordance with an example embodiment of the present disclosure

All-Atomistic MD Simulation Technique:

Structure Densification and Equilibration:

The structure presented in FIG. 3 was densified by NPT equilibration. The initial structure was sparse and full of empty space. However, during the course of densification by NPT equilibration, the density of the local structure increased to 0.865 g/cc, which is close to within 5% of the experimentally measured density in the conventional/traditional methods. The densified crosslinked SBR structure is depicted in FIG. 4. FIG. 4, with reference to FIGS. 1 through 3, depicts an all-atomistic structure of densified crosslinked SBR rubber system in accordance with an example embodiment of the present disclosure. More particularly, a crosslinked unfilled SBR 1502 rubber has been analysed in FIG. 4. However, a second system has been created having a composite structure of spherical particles dispersed in polymer matrix. FIG. 5, with reference to FIGS. 1 through 4, depicts an all-atomistic local structure of a densified particle filled rubber matrix composite in accordance with an example embodiment of the present disclosure. More particularly, FIG. 5 shows an all-atomistic model of such a composite system with 3 carbon-like filler particles with 60 nm diameter dispersed in rubber matrix. The filler particles are hollow spheres and possess a density close to that of carbon-black filler commonly used in tyre rubber.

Figure 6:
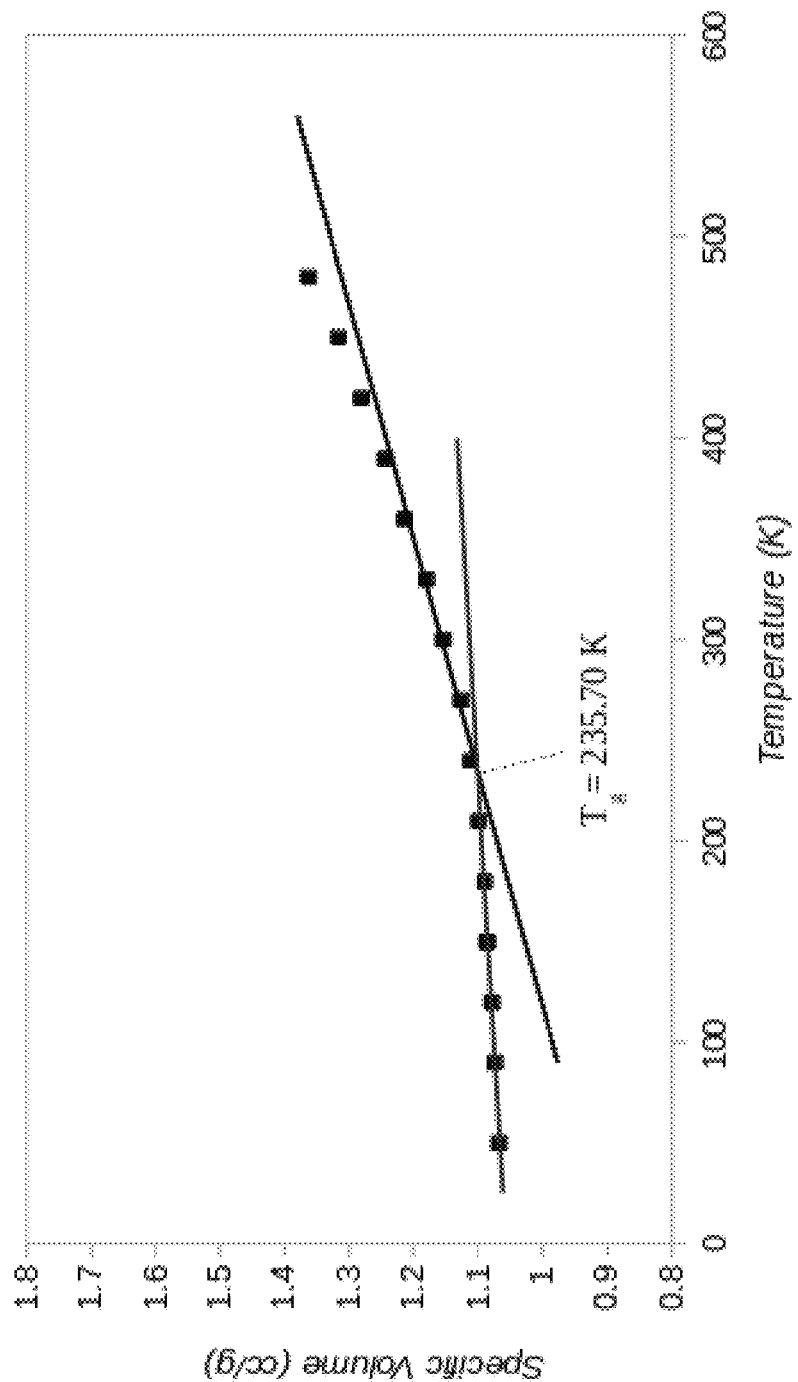
FIG. 6 depicts a graphical representation of specific volume vs. temperature curve for calculating Glass transition temperature (GTT) and Coefficient of thermal expansion (COTE) in accordance with an example embodiment of the present disclosure

Thermal Properties:

The crosslinked SBR single-phase system has been subjected to NPT equilibration again at different temperatures (50-450 K) for 1.5 ns of all-atomistic MD run for their thermal properties. The equilibrium specific volume is plotted against temperature as depicted in FIG. 6. More specifically, FIG. 6, with reference to FIGS. 1 through 5, depicts a graphical representation of Specific volume vs. temperature curve for calculating GTT and COTE in accordance with an example embodiment of the present disclosure. FIG. 6 depicts two different slopes in the left and right hand side, corresponding to the glassy and rubbery behaviour. The intersection of the two slopes give the glass transition temperature (GTT). From the slopes of the fitted straight lines, values of volume coefficient of thermal expansion (COTE) can be calculated. In this case study, the calculated GTT from MD simulation was 235.7 K, whereas the experimental value was 237.5 K, close to within 0.76%.

Figure 7:
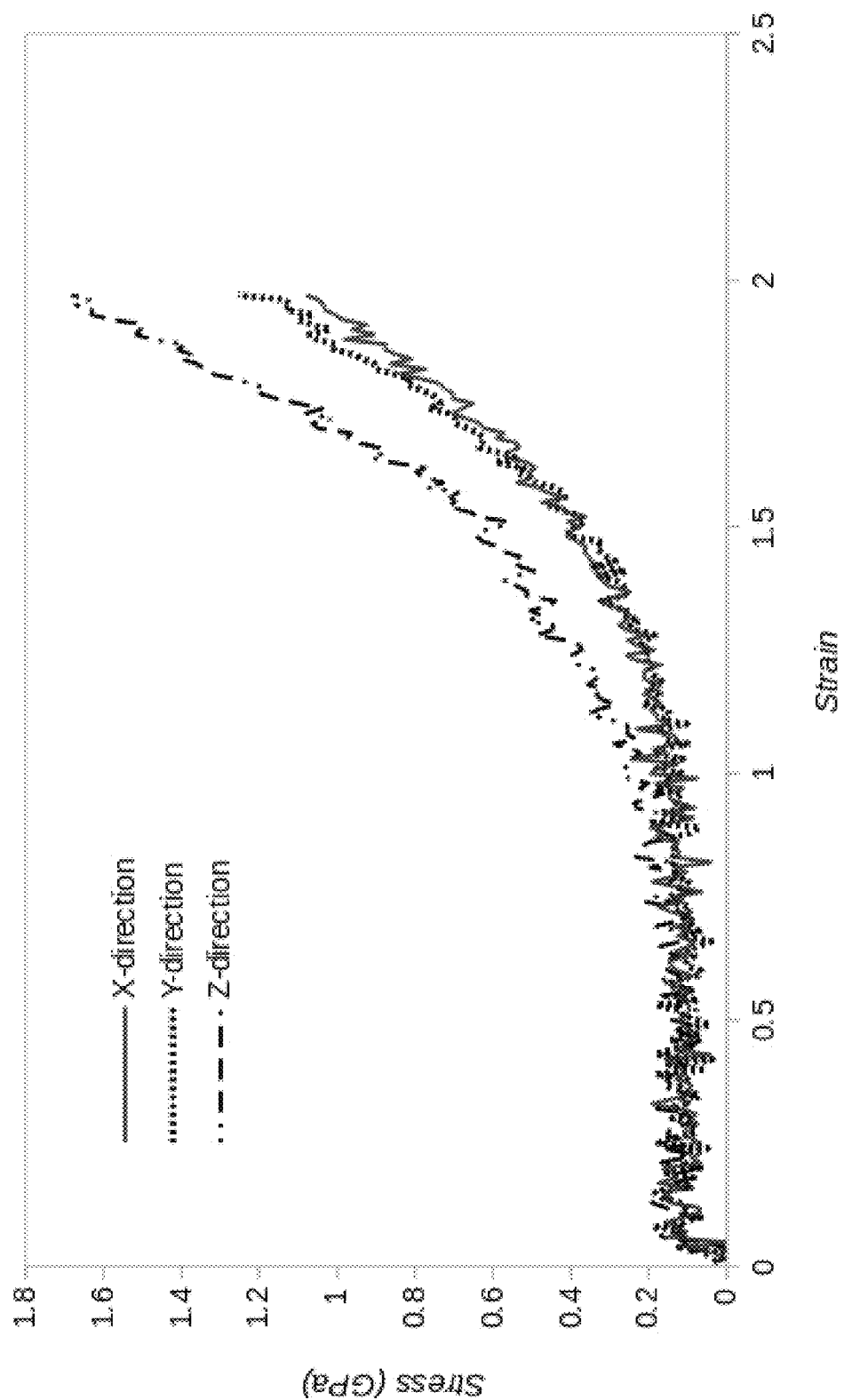
FIG. 7 depicts a graphical representation of Non-equilibrium molecular dynamics (NEMD) high strain-rate stress-strain of a styrene butadiene rubber (SBR) carried out along 3 axes in accordance with an example embodiment of the present disclosure.
Figure 8:
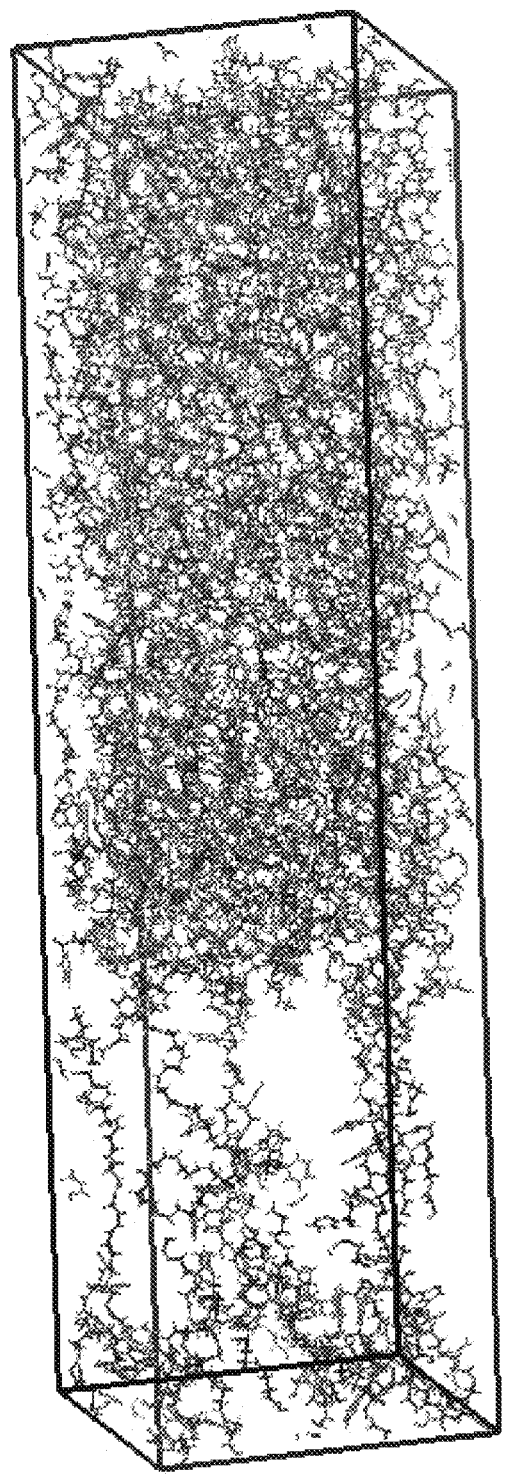
FIG. 8 depicts local fracture in NEMD all-atomistic simulation of a crosslinked SBR system in accordance with an example embodiment of the present disclosure.

Non-Equilibrium Molecular Dynamics (NEMD):

After obtaining the equilibrium local structure and thermal properties, the simulated systems are tested for their mechanical properties responses. First an equilibrated system is subjected to a large strain at large strain rate ($10^7$-$10^{11}$/sec) along the three principal directions. One of such a simulation carried out at a strain rate of $10^{10}$/sec by non-equilibrium molecular dynamics (NEMD) along X, Y and Z directions is depicted in FIG. 7. More particularly, FIG. 7, with reference to FIGS. 1 through 6, depicts a graphical representation of NEMD high strain-rate stress-strain of SBR carried out along 3 axes in accordance with an example embodiment of the present disclosure. The system was loaded from 3 different axes (X, Y, and Z directions as depicted in FIG. 7) mainly to check the isotropic nature of the crosslinked rubber system. It can be observed that the nature of the NEMD stress-strain curve and the stress values are very close to each other irrespective of the loading directions, showing isotropic mechanical properties of the system.

Nano Fracture NEMD:

By applying NEMD, the simulated system can be stretched to such an extent that the local structure undergoes tearing/fracture/cavity formation. This happens when a large strain is applied and local deformation causes tearing of the matrix or matrix-filler interface. This is illustrated/depicted in FIG. 8, where only a few crosslinked polymer chains are bearing the applied stress and Nano-cavity forms. This simulation helps in estimating tear strength/fracture strength. More particularly, FIG. 8, with reference to FIGS. 1 through 7, depicts local fracture in NEMD all-atomistic simulation of crosslinked SBR system in accordance with an example embodiment of the present disclosure.

Figure 9:
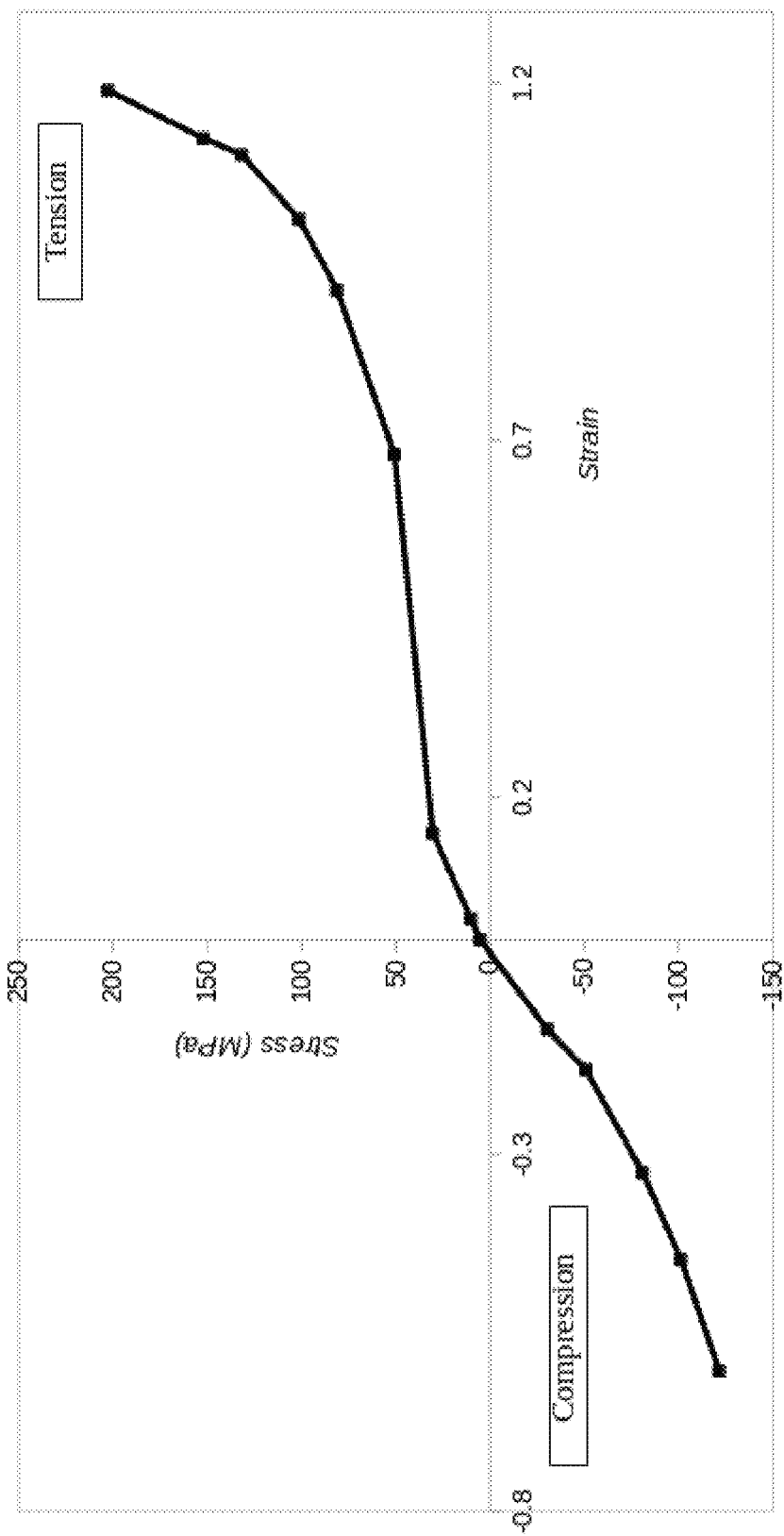
FIG. 9 depicts a graphical representation illustrating a stress-strain behaviour for a crosslinked SBR system for instantaneous relaxation both in tensile and compressive stress in accordance with an example embodiment of the present disclosure.
Figure 10:
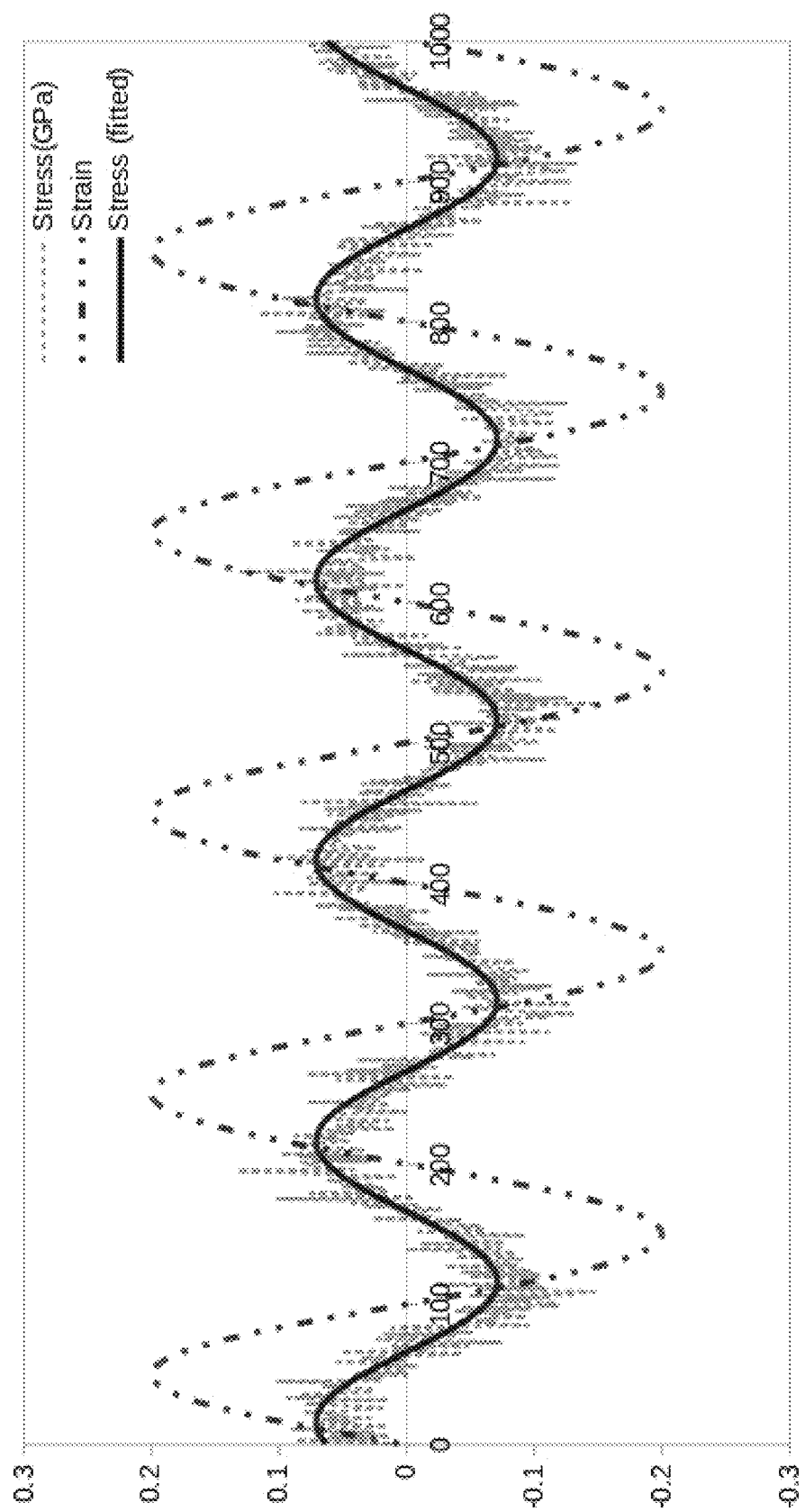
FIG. 10 depicts a graphical representation illustrating stress response for cyclic tensile loading in a SBR system in accordance with an example embodiment of the present disclosure.

Pressure Response:

By carrying out equilibrium NPT simulation under different applied pressures, change of volume of the simulation cell can be observed. However, in all-atomistic MD simulations, the run time is generally bound to only a few Nano-seconds. This pressure response simulations only help in instantaneous relaxation behaviour of polymer systems. FIG. 9, with reference to FIGS. 1 through 8, depicts a graphical representation illustrating a stress-strain behaviour for crosslinked SBR system for instantaneous relaxation both in tensile and compressive stress in accordance with an example embodiment of the present disclosure. More particularly, FIG. 9 depicts an instantaneous pressure response stress-strain curve for all-atomistic simulation of crosslinked SBR system. It can be noted that the stress response magnitudes in this type of simulations are orders of magnitude lower than the NEMD stress-strain simulations (FIG. 3). This system was equilibrated for a maximum of 5 ns of actual simulation time.

Cyclic Stress-Strain and Dynamic Mechanical Analysis (DMA):

In this kind of simulations, the model system is subjected to oscillatory cyclic sinusoidal strain (uniaxial or shear). The stress response is also cyclic sinusoidal in nature, but with a phase difference δ between the stress and the strain. Hereby a cyclic/dynamic mechanical analysis of stress-strain on crosslinked SBR system is given in FIG. 10. More particularly, FIG. 10, with reference to FIGS. 1 through 9, depicts a graphical representation illustrating stress response for cyclic tensile loading in SBR system in accordance with an example embodiment of the present disclosure. From fitting the stress response w.r.t. the strain, important DMA properties for example, but are not limited to, storage, loss moduli and tan (δ) can be obtained. In this case, the loading cycle frequency was $5*10^9$ Hz with a strain amplitude of 0.2.

Figure 11A:
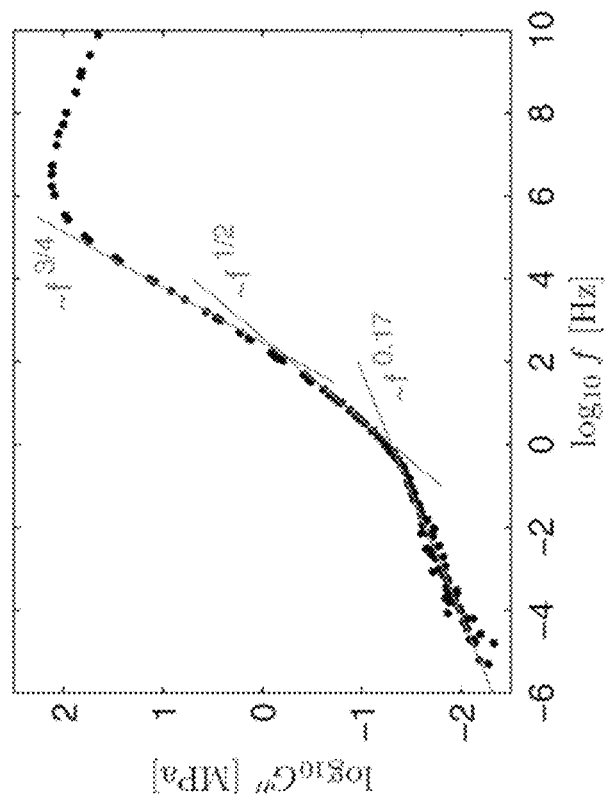
FIG. 11A depicts graphical representations illustrating DMA frequency response for storage and loss shear moduli (G' and G") of crosslinked unfilled SBR at reference temperature 25° C. obtained from experiments obtained from conventional procedures in accordance with an example embodiment of the present disclosure.
Figure 11A:
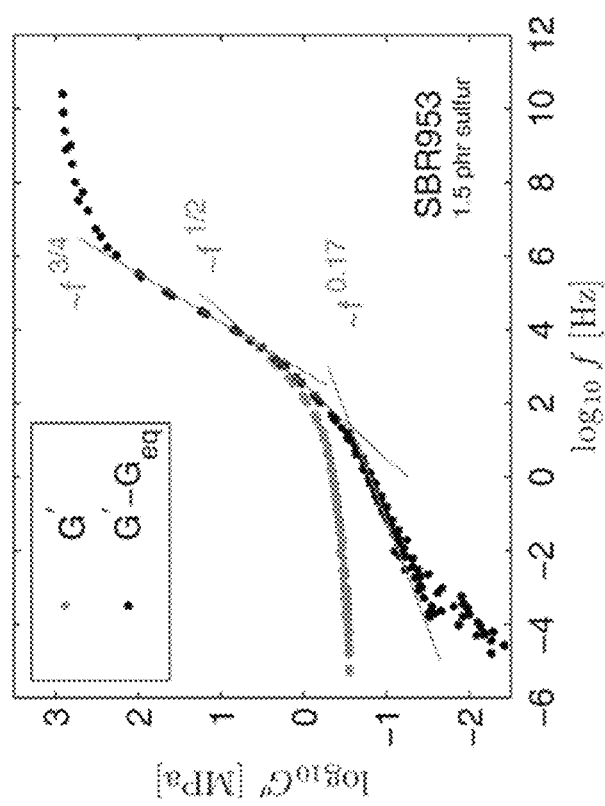
Figure 11B:
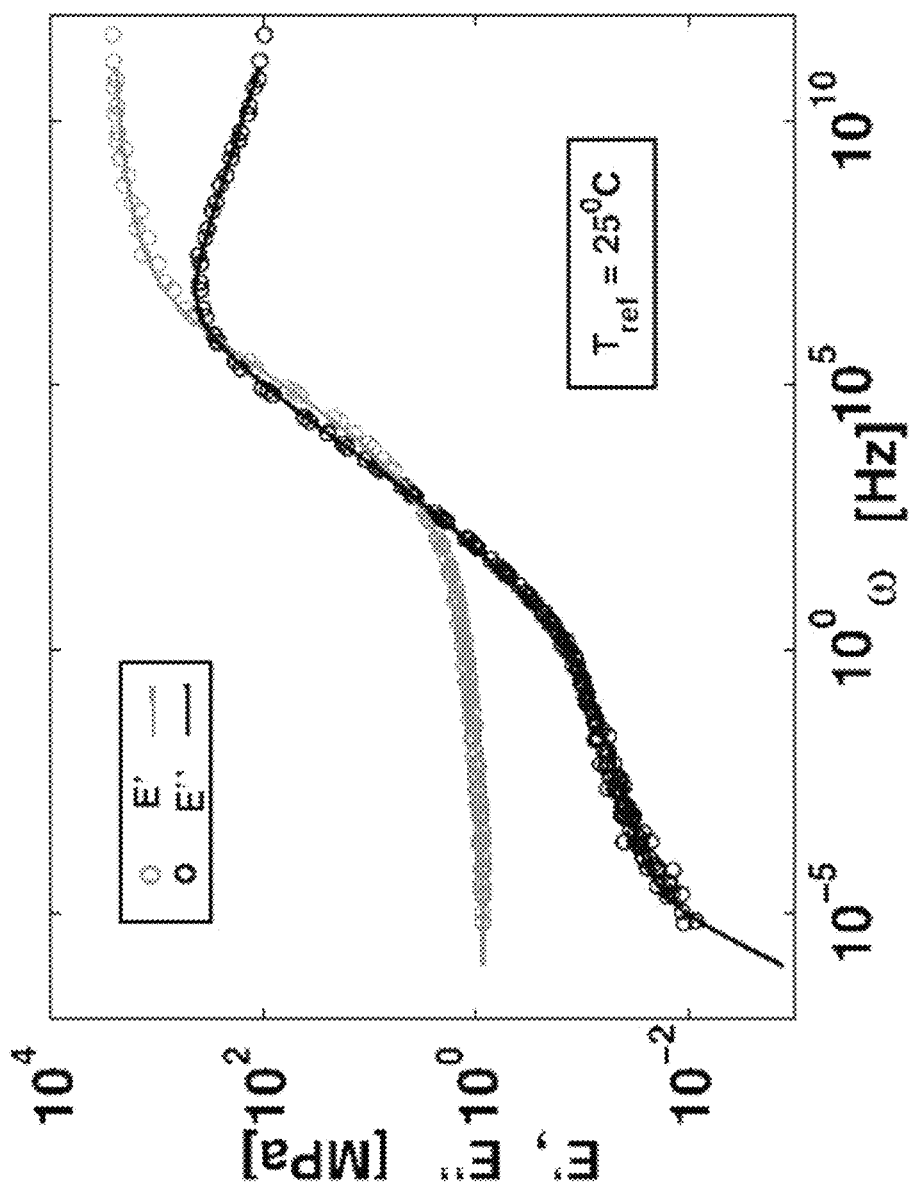
FIG. 11B depicts a graphical representation illustrating DMA frequency response for storage and loss tensile moduli (E' and E") obtained from experiments obtained from conventional procedures in accordance with an example embodiment of the present disclosure.

DMA and Frequency Response:

With the help of time-temperature superposition (TTS) principle the DMA experiments/simulations carried out at different frequency and temperatures can be arranged as frequency dependent DMA at a particular reference temperature. FIG. 11A, with reference to FIGS. 1 through 10, depicts graphical representations illustrating DMA frequency response for storage and loss shear moduli (G' and G") of crosslinked unfilled SBR at reference temperature 25° C. obtained from experiments obtained from conventional procedures in accordance with an example embodiment of the present disclosure. Similarly FIG. 11B, with reference to FIGS. 1 through 11A, depicts a graphical representation illustrating DMA frequency response for storage and loss tensile moduli (E' and E") obtained from experiments obtained from conventional procedures in accordance with an example embodiment of the present disclosure.

Figure 12:
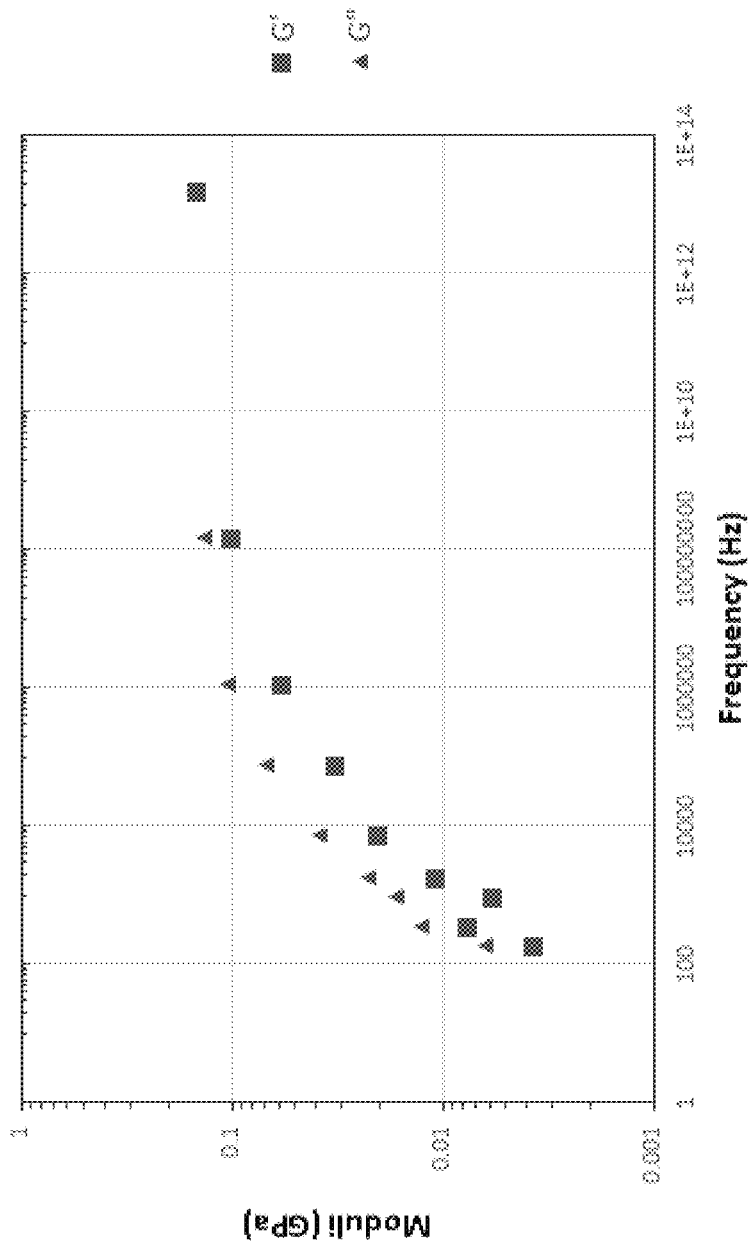
FIG. 12 depict a graphical representation illustrating simulated DMA plot for storage and loss moduli w.r.t. wide frequency range at a reference temperature of 5.7° C. in accordance with an example embodiment of the present disclosure.
Figure 13:
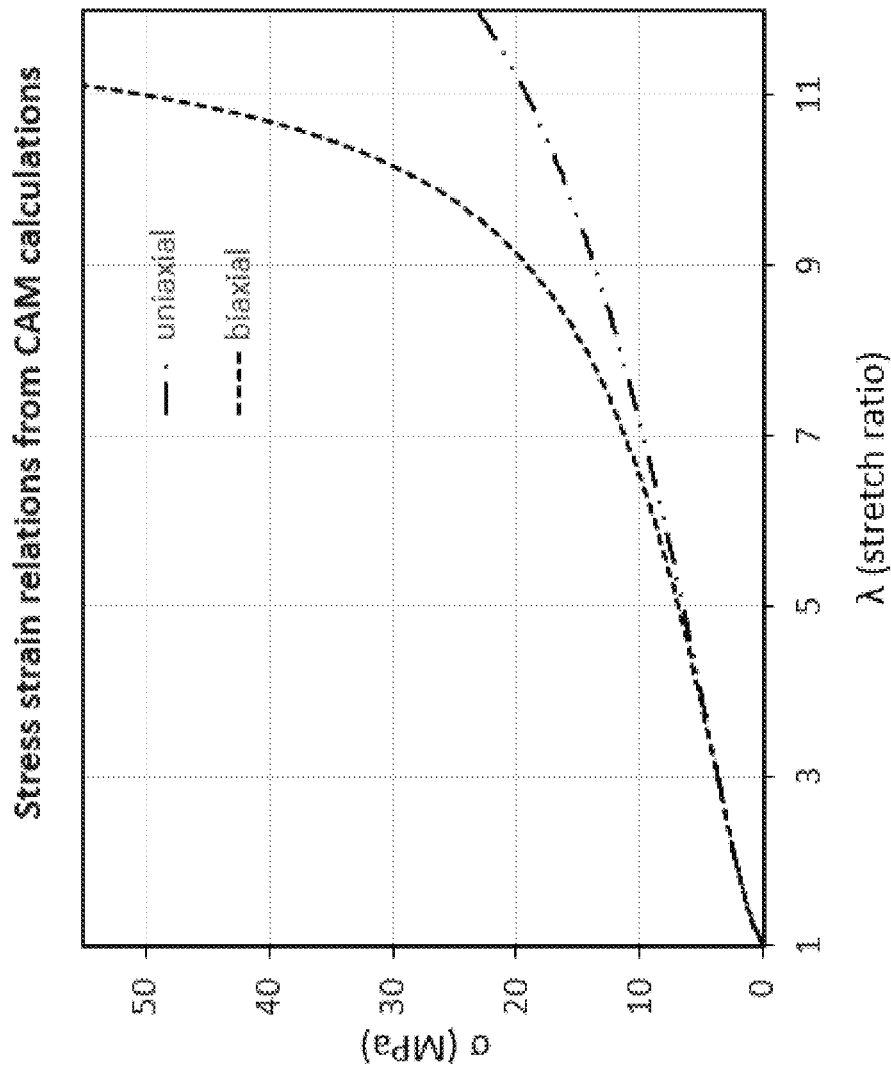
FIG. 13 depicts a graphical representation illustrating equilibrium stress-strain relationships curves under uniaxial and equibiaxial loading for SBR by one or more CAM simulation technique(s) in accordance with an example embodiment of the present disclosure.

DMA analysis w.r.t. wide frequency range was carried out by utilizing different simulation methods. First dynamic cyclic stress-strain analysis was carried at a fixed frequency of $5*10^9$ Hz and for a temperature range of 200-800 K. Next, TTS principle along with the calculated GTT was utilized to plot the DMA storage and loss moduli w.r.t. wide frequency range at a reference temperature of 5.7° C. This graph is plotted in FIG. 12 in log-log scale. More particularly, FIG. 12, with reference to FIGS. 1 through 11B, depict a graphical representation illustrating simulated DMA plot for storage and loss moduli w.r.t. wide frequency range at a reference temperature of 5.7° C. in accordance with an example embodiment of the present disclosure. When compared with the experiment generated graphs as in FIGS. 11A and 11B, it can be seen that the trends of the simulated DMA moduli in FIG. 12 are quite similar. For lower frequency equilibrium loading-like situations, constitutive analytical method (CAM) can be combined along with this all-atomistic DMA analysis.

Constitutive Analytical Modelling (CAM):

In this study CAM simulation technique's output (or data) was utilized to calculate the stress-strain behaviour of equilibrium loading conditions. At this current phase stress-strain curves and their corresponding elastic moduli were calculated for uniaxial, equibiaxial and pure shear type loading. From all-atomistic MD simulations, few parameters such as volume of the crosslinked rubber, number of crosslinked polymer segments and number of linking elements (Kuhn lengths) per polymer segments between Sulphur crosslinking points and temperature are passed on as input. The stress-strain graphs were obtained by statistical-mechanics based analytical analysis methods of crosslinked polymers (as known in the art). The calculated stress-strain curves are plotted in FIG. 13. More particularly, FIG. 13, with reference to FIGS. 1 through 12, depicts a graphical representation illustrating equilibrium stress-strain relationships curves under uniaxial and equibiaxial loading for SBR by one or more CAM simulation technique(s) in accordance with an example embodiment of the present disclosure. The elastic moduli can be obtained by taking the initial slope of the stress-strain curves. The nature and shape of the stress-strain curves (engineering stress versus stretch ratio) resemble that of experimental curves on different kinds of rubbers reported in the conventional method(s).

Coarse-Graining MD (CGMD) Simulation Technique:

In CGMD simulations, more than 10 atoms of a few adjacent monomers are clubbed/merged together as a coarse bead. This treatment effectively can allow to simulate 100 times bigger systems than that possible by all-atomistic MD. In this case study some trial structural configurations were also studied to resemble the behaviour of crosslinked rubber. The interaction potentials for the coarse-graining particles are initially inspired techniques known in the art and the finite extensible nonlinear elasticity (FENE) formulation was adopted combined with LJ non-bonded interactions. The potentials were fine-tuned to resemble some of the properties obtained from all-atomistic MD like the density, redial distribution function (RDF) DMA analysis etc. However, some of the first simulation results are presented here with an attempt to bridge sub-micrometer length-scales.

Figure 14:
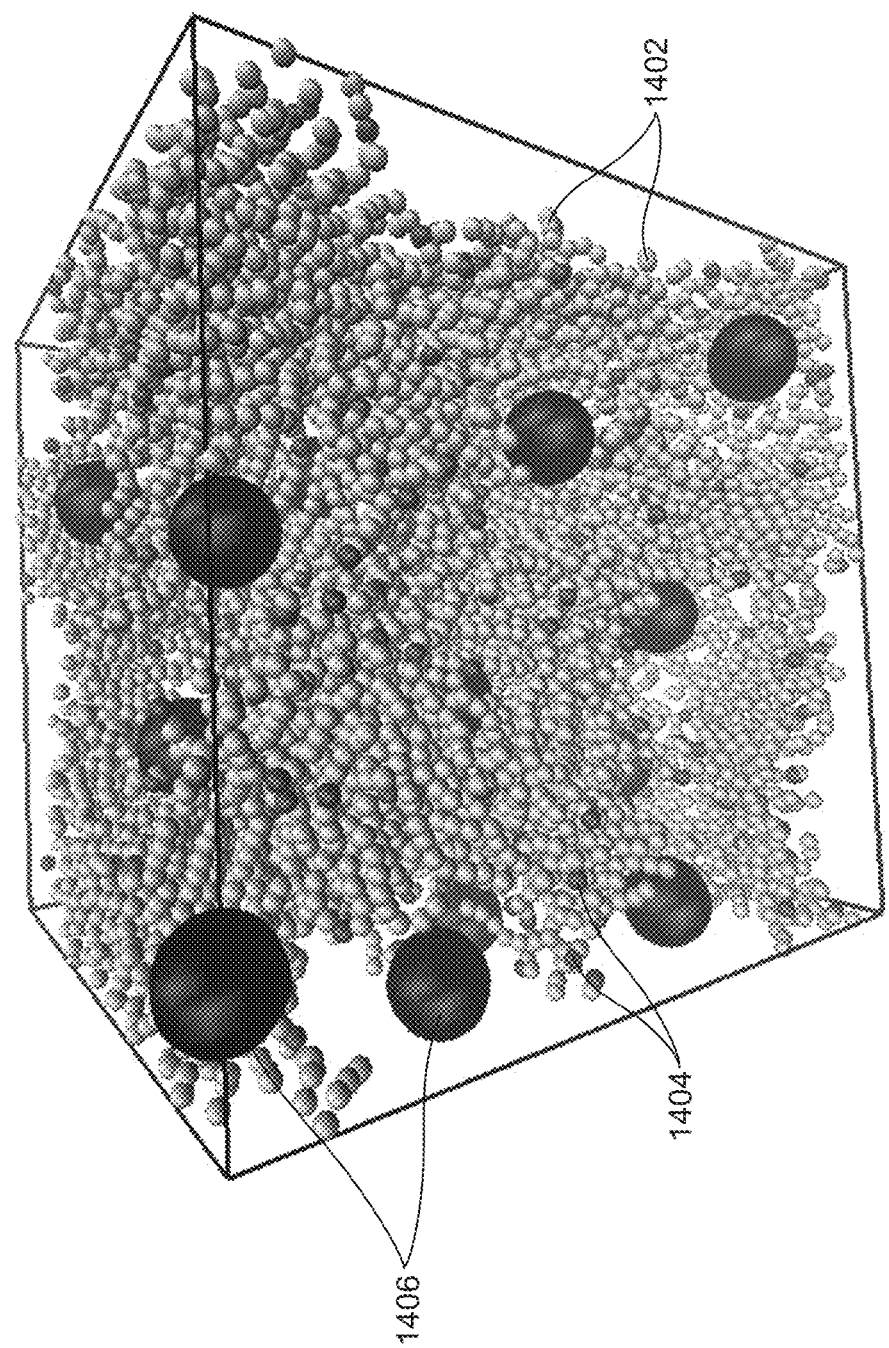
FIG. 14 depicts a CGMD densified structure of nanoparticle dispersed crosslinked polymer matrix composite in accordance with an example embodiment of the present disclosure.
Figure 15:
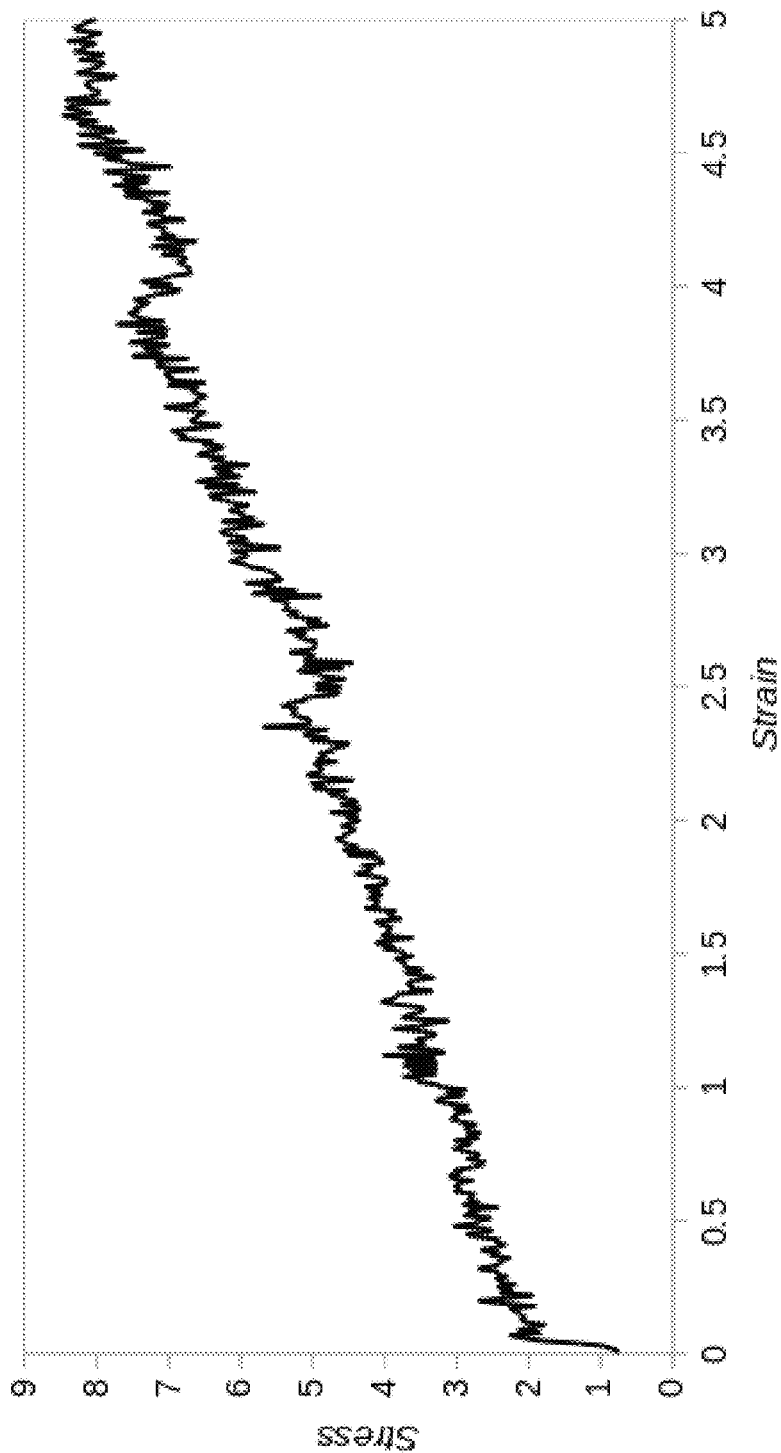
FIG. 15 depict a graphical representation illustrating a CGMD NEMD curve of crosslinked unfilled rubber system in accordance with an example embodiment of the present disclosure.

CGMD Densified Composite Structure:

Initially some polymer chains consisting of 30 beads each and 5 adjacent sulphur beads are constructed with a very low density. Some bigger nanoparticle beads are also inserted with different kind of interaction potentials. Then the system was subjected to NPT equilibration densification and the following structure was obtained as depicted in FIG. 14. More particularly, FIG. 14, with reference to FIGS. 1 through 13, depicts a CGMD densified structure of nanoparticle dispersed crosslinked polymer matrix composite in accordance with an example embodiment of the present disclosure. The small gray color beads (denoted by 1402 in FIG. 14) belong to the polymer-chains, small black beads (denoted by 1404 in FIG. 14) are crosslinked Sulphur molecules and big black beads (denoted by 1406 in FIG. 14) are the dispersed filler particles. It can be observed that both the crosslinker beads and the filler beads are well dispersed throughout the whole structure.

Figure 16:
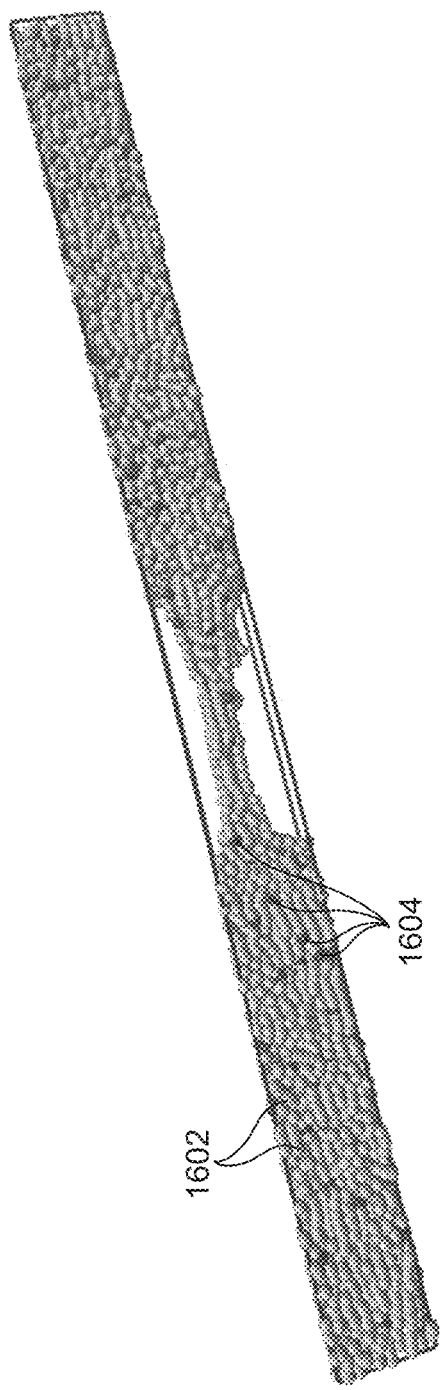
FIG. 16 depicts a local fracture and tearing in CGMD NEMD of unfilled crosslinked polymer system in accordance with an example embodiment of the present disclosure.

CGMD NEMD and Local Fracture:

Similar to the all-atomistic MD, the CGMD simulated system was also subjected to finite strain rate NEMD loading simulations. The stress response with applied strain is plotted in FIG. 15. It can be noted that after a certain strain, there are kinks in the curve as depicted in graphical representation of FIG. 15. More particularly, FIG. 15, with reference to FIGS. 1 through 14, depict a graphical representation illustrating a CGMD NEMD curve of crosslinked unfilled rubber system in accordance with an example embodiment of the present disclosure. This corresponds to the initiation of local fracture in the crosslinked rubber system as shown in FIG. 16. More particularly, FIG. 16, with reference to FIGS. 1 through 15, depicts a local fracture and tearing in CGMD NEMD of unfilled crosslinked polymer system in accordance with an example embodiment of the present disclosure. It can be seen that fracture is rather localized with stress concentrated only on a few polymer strands with Nano-cavity surrounding it. The small gray color beads (denoted by 1602 in FIG. 16) belong to the polymer-chains, small black beads (denoted by 1604 in FIG. 16) are crosslinked Sulphur molecules.

Figure 17:
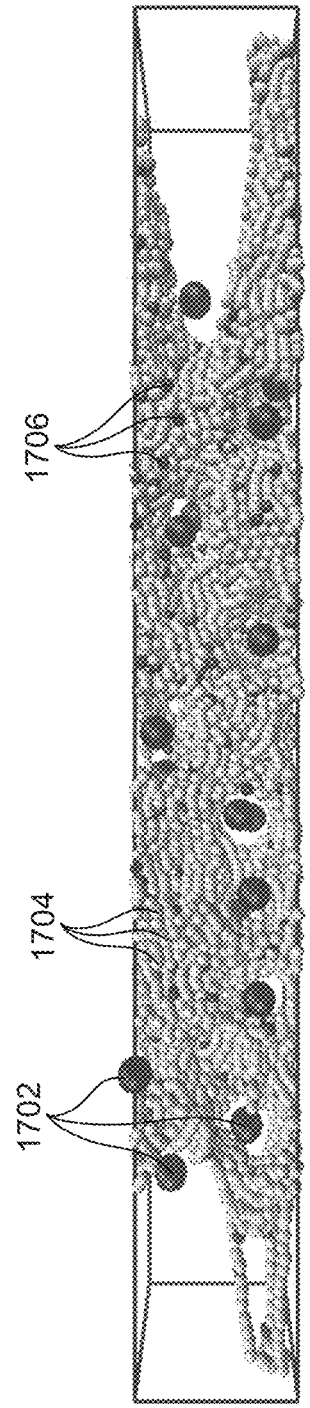
FIG. 17 depicts a local fracture and tearing in CGMD NEMD of particle filled crosslinked polymer matrix composite system in accordance with an example embodiment of the present disclosure.

In addition to the CGMD NEMD stretching of unfilled crosslinked polymer, another system was also studied in the same manner but with the filler particles dispersed into the crosslinked polymer matrix. While stretching after a certain high strain, the system showed tearing/fracture and cavitation behaviour as shown in FIG. 17, where big black beads (denoted by 1702 in FIG. 17) are the filler particles, small gray color beads (denoted by 1704 in FIG. 17) belong to the polymer-chains, small black beads (denoted by 1706 in FIG. 17) are crosslinked Sulphur molecules. More particularly, FIG. 17, with reference to FIGS. 1 through 17, depicts a local fracture and tearing in CGMD NEMD of particle filled crosslinked polymer matrix composite system in accordance with an example embodiment of the present disclosure. It can be observed that after the fracture has initiated, only a few polymer chains are essentially bearing the load. Also few filler particles have come out to the fractured surface. The filler particles which were initially dispersed in the polymer matrix, shows a little tendency of agglomeration upon given a large deformation. This is how the local structure changes are captured by the simulation of larger crosslinked polymer matrix composite structure by CGMD.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A computer implemented method, comprising:

obtaining information pertaining to composite materials, wherein the information comprises at least one or more molecular and one or more nano-scale components of a polymer structure;

simulating, using an All-Atomistic Molecular Dynamics (MD) simulation technique, the information pertaining to the one or more molecular and the one or more nano-scale components to obtain simulated data, wherein the simulated data represents an initial input structure for multiscale modelling of the polymer;

performing, using the All-Atomistic MD simulation technique, (i) a structural densification on the simulated data to obtain a densified polymer structure output, and (ii) an equilibration technique on the densified polymer structure output to determine an equilibration of the polymer structure, wherein the structural densification is performed by constant temperature-pressure (NPT) equilibration technique;

simulating the densified polymer structure output to determine at least (i) one of one or more relevant mechanical properties from a set of mechanical properties, (ii) one of one or more relevant thermal properties from a set of thermal properties, and (iii) one of one or more thermodynamic properties, wherein the relevant thermal properties are determined by subjecting the densified polymer structure output to different temperatures ranging from 50 K to 450 K, and wherein the determined one or more relevant mechanical properties are analyzed to determine storage modulus (G'), loss modulus (G"), and tan ($\delta$) loss factor of the densified polymer structure using dynamic mechanical analysis (DMA);

performing, a Constitutive Analytical Modeling (CAM) simulation technique, on the determined one or more relevant mechanical properties to obtain one or more CAM outputs based on input parameters comprising volume of crosslinked polymer structure, number of polymer segments and number of crosslinkers per polymer chain in the polymer structure;

performing, a Coarse Grain Molecular Dynamics (CGMD) simulation technique, on (i) the one or more relevant mechanical properties and the one or more relevant thermal properties determined from the All-Atomistic MD simulation, (ii) the one or more CAM outputs, and (iii) the one or more thermodynamic properties determined from the All-Atomistic MD simulation, to generate one or more CGMD outputs; and performing, a Finite Element Analysis (FEA) modeling, on at least (i) some of the one or more relevant mechanical properties and the one or more relevant thermal properties, (ii) some of the one or more CAM outputs, and (iii) some of the one or more CGMD outputs to predict a behaviour of the polymer structure, wherein the densified polymer structure output and equilibration are provided as inputs for performing the FEA modeling, and wherein the behaviour of the polymer structure is predicted from FEA outputs including structural response at macro level, design optimization based on local microstructure, design validation through experimentation, interfacial failure through cohesive analysis, and damage and failure analysis.

2. The method of claim 1, wherein the one or more relevant mechanical properties from a set of mechanical properties comprise Non-equilibrium molecular dynamics (NEMD) and Nano fracture, cyclic stress-strain, pressure response, Nano-filler dispersion, and phase-interface strength.

3. The method of claim 1, wherein the one or more relevant thermal properties from the set of thermal properties comprise thermal expansion, heat conduction and phonon, and wherein the one or more thermodynamic properties comprise thermodynamics derived cohesive energy.

4. The method of claim 1, wherein the one or more CAM outputs comprise equilibrium stress-strain and elastic moduli, cyclic loading analysis of polymer matrix composites, Payne and Mullins effects, stress-strain hysteresis with one or more strain rates.

5. The method of claim 1, wherein the one or more CGMD outputs comprise equilibrium and non-equilibrium stress-strain relationships, Dynamic mechanical analysis (DMA), local micro structural evolution, localized fracture, Radial distribution function (RDF) and Glass transition temperature (GTT), and one or more inputs for Dissipative particle dynamics-CGMD (DPD-CGMD) simulation technique.

6. A system, comprising:
a memory storing instructions;
one or more communication interfaces; and
one or more hardware processors coupled to the memory via the one or more communication interfaces, wherein the one or more hardware processors are configured by the instructions to:
obtain, information pertaining to composite materials, wherein the information comprises at least one or more molecular and one or more nano-scale components of a polymer structure;
simulate, using an All-Atomistic Molecular Dynamics (MD) simulation technique, the information pertaining to the one or more molecular and the one or more nano-scale components to obtain simulated data, wherein the simulated data represents an initial input structure for multiscale modelling of the polymer;
perform, using the All-Atomistic MD simulation technique, (i) a structural densification on the simulated data to obtain a densified polymer structure output, and (ii) an equilibration technique on the densified polymer structure output to determine an equilibration of the polymer structure, wherein the structural densification is performed by constant temperature-pressure (NPT) equilibration technique;
simulate the densified polymer structure output to determine at least (i) one of one or more relevant mechanical properties from a set of mechanical properties, (ii) one of one or more relevant thermal properties from a set of thermal properties, and (iii) one of one or more thermodynamic properties, wherein the relevant thermal properties are determined by subjecting the densified polymer structure output to different temperatures ranging from 50 K to 450 K, and wherein the determined one or more relevant mechanical properties are analyzed to determine storage modulus (G'), loss modulus (G''), and tan ($\delta$) loss factor of the densified polymer structure using dynamic mechanical analysis (DMA);
perform, a Constitutive Analytical Modeling (CAM) simulation technique, on the determined one or more relevant mechanical properties to obtain one or more CAM outputs based on input parameters comprising volume of crosslinked polymer structure, number of polymer segments and number of crosslinkers per polymer chain in the polymer structure;
perform, a Coarse Grain Molecular Dynamics (CGMD) simulation technique, on (i) the one or more relevant mechanical properties and the one or more relevant thermal properties determined from the All-Atomistic MD simulation, (ii) the one or more CAM outputs, and (iii) the one or more thermodynamic properties determined from the All-Atomistic MD simulation to generate one or more CGMD outputs; and
perform, a Finite Element Analysis (FEA) modeling, on at least (i) some of the one or more relevant mechanical properties and the one or more relevant thermal properties, (ii) some of the one or more CAM outputs, and (iii) some of the one or more CGMD outputs to predict a behaviour of the polymer structure, wherein the densified polymer structure output and equilibration are provided as inputs for performing the FEA modeling, and wherein the behaviour of the polymer structure is predicted from FEA outputs including structural response at macro level, design optimization based on local microstructure, design validation through experimentation, interfacial failure through cohesive analysis, and damage and failure analysis.

7. The system of claim 6, wherein the one or more relevant mechanical properties from a set of mechanical properties comprise Non-equilibrium molecular dynamics (NEMD) and Nano fracture, cyclic stress-strain, pressure response, Nano-filler dispersion, and phase-interface strength.

8. The system of claim 6, wherein the one or more relevant thermal properties from the set of thermal properties comprise thermal expansion, heat conduction and phonon, and wherein the one or more thermodynamic properties comprise thermodynamics derived cohesive energy.

9. The system of claim 6, wherein the one or more CAM outputs comprise equilibrium stress-strain relationships and elastic moduli, cyclic loading analysis of polymer matrix composites, Payne and Mullins effects, stress-strain hysteresis with one or more strain rates.

10. The system of claim 6, wherein the one or more CGMD outputs comprise equilibrium and non-equilibrium stress-strain relationships, Dynamic mechanical analysis (DMA), local micro structural evolution, localized fracture, Radial distribution function (RDF) and Glass transition temperature (GTT), and one or more inputs for Dissipative particle dynamics-CGMD (DPD-CGMD) simulation technique.

11. One or more non-transitory machine readable information storage mediums comprising one or more instructions which when executed by one or more hardware processors cause:
obtaining information pertaining to composite materials, wherein the information comprises at least one or more molecular and one or more nano-scale components of a polymer structure;

simulating, using an All-Atomistic Molecular Dynamics (MD) simulation technique, the information pertaining to the one or more molecular and the one or more nano-scale components to obtain simulated data, wherein the simulated data represents an initial input structure for multiscale modelling of the polymer;

performing, using the All-Atomistic MD simulation technique, (i) a structural densification on the simulated data to obtain a densified polymer structure output, and (ii) an equilibration technique on the densified polymer structure output to determine an equilibration of the polymer structure, wherein the structural densification is performed by constant temperature-pressure (NPT) equilibration technique;

simulating the densified polymer structure output to determine at least (i) one of one or more relevant mechanical properties from a set of mechanical properties, (ii) one of one or more relevant thermal properties from a set of thermal properties, and (iii) one of one or more thermodynamic properties, wherein the relevant thermal properties are determined by subjecting the densified polymer structure output to different temperatures ranging from 50 K to 450 K, and wherein the determined one or more relevant mechanical properties are analyzed to determine storage modulus (G'), loss modulus (G"), and tan ($\delta$) loss factor of the densified polymer structure using dynamic mechanical analysis (DMA);

performing, a Constitutive Analytical Modeling (CAM) simulation technique, on the determined one or more relevant mechanical properties to obtain one or more CAM outputs based on input parameters comprising volume of crosslinked polymer structure, number of polymer segments and number of crosslinkers per polymer chain in the polymer structure performing, a Coarse Grain Molecular Dynamics (CGMD) simulation technique, on (i) the one or more relevant mechanical properties and the one or more relevant thermal properties determined from the All-Atomistic MD simulation, (ii) the one or more CAM outputs, and (iii) the one or more thermodynamic properties determined from the All-Atomistic MD simulation to generate one or more CGMD outputs; and performing, a Finite Element Analysis (FEA) modeling, on at least (i) some of the one or more relevant mechanical properties and the one or more relevant thermal properties, (ii) some of the one or more CAM outputs, and (iii) some of the one or more CGMD outputs to predict a behaviour of the polymer structure, wherein the densified polymer structure output and equilibration are provided as inputs for performing the FEA modeling, and wherein the behaviour of the polymer structure is predicted from FEA outputs including structural response at macro level, design optimization based on local microstructure, design validation through experimentation, interfacial failure through cohesive analysis, and damage and failure analysis.

12. The one or more non-transitory machine readable information storage mediums of claim 11, wherein the one or more relevant mechanical properties from a set of mechanical properties comprise Non-equilibrium molecular dynamics (NEMD) and Nano fracture, cyclic stress-strain, pressure response, Nano-filler dispersion, and phase-interface strength.

13. The one or more non-transitory machine readable information storage mediums of claim 11, wherein the one or more relevant thermal properties from the set of thermal properties comprise thermal expansion, heat conduction and phonon, and wherein the one or more thermodynamic properties comprise thermodynamics derived cohesive energy.

14. The one or more non-transitory machine readable information storage mediums of claim 11, wherein the one or more CAM outputs comprise equilibrium stress-strain and elastic moduli, cyclic loading analysis of polymer matrix composites, Payne and Mullins effects, stress-strain hysteresis with one or more strain rates.

15. The one or more non-transitory machine readable information storage mediums of claim 11, wherein the one or more CGMD outputs comprise equilibrium and non-equilibrium stress-strain relationships, Dynamic mechanical analysis (DMA), local micro structural evolution, localized fracture, Radial distribution function (RDF) and Glass transition temperature (GTT), and one or more inputs for Dissipative particle dynamics CGMD (DPD-CGMD) simulation technique.

* * * * *